United States Patent [19]

Gruenfeld

[11] Patent Number: 4,479,963
[45] Date of Patent: * Oct. 30, 1984

[54] 1-CARBOXYALKANOYLINDOLINE-2-CARBOXYLIC ACIDS

[75] Inventor: Norbert Gruenfeld, White Plains, N.Y.

[73] Assignee: Ciba-Geigy Corporation, Ardsley, N.Y.

[ * ] Notice: The portion of the term of this patent subsequent to Feb. 22, 2000 has been disclaimed.

[21] Appl. No.: 371,700

[22] Filed: Apr. 26, 1982

Related U.S. Application Data

[63] Continuation-in-part of Ser. No. 235,294, Feb. 17, 1981, Pat. No. 4,374,847, which is a continuation-in-part of Ser. No. 200,706, Oct. 27, 1980, abandoned.

[51] Int. Cl.$^3$ ............... A61K 31/40; C07D 209/42
[52] U.S. Cl. ............... 424/274; 260/245.7; 424/263; 424/267; 546/187; 546/193; 546/194; 546/201; 546/256; 546/273; 548/430; 548/455; 548/463; 548/465; 548/468; 548/491
[58] Field of Search ............... 548/430, 491, 465, 468, 548/455, 463; 546/187, 193, 194, 201, 256, 273; 260/245.7; 424/263, 267, 274

[56] References Cited

U.S. PATENT DOCUMENTS

| | | | |
|---|---|---|---|
| 3,780,062 | 12/1973 | Kaiser et al. | 548/491 |
| 3,796,723 | 3/1974 | Kaiser et al. | 260/326.11 |
| 3,974,145 | 8/1976 | Kimura et al. | |
| 4,046,889 | 9/1977 | Ondetti et al. | 424/244 |
| 4,052,511 | 10/1977 | Cushman et al. | 424/274 |
| 4,154,937 | 4/1979 | Cushman et al. | 546/221 |
| 4,303,583 | 12/1981 | Kim et al. | 260/239.3 |
| 4,311,705 | 1/1982 | Ondetti et al. | 424/274 |
| 4,350,633 | 9/1982 | Kim et al. | 424/274 |
| 4,374,847 | 2/1983 | Gruenfeld | 548/491 |
| 4,404,206 | 9/1983 | Vincent et al. | 424/258 |

FOREIGN PATENT DOCUMENTS

| | | |
|---|---|---|
| 0024852 | 3/1981 | European Pat. Off. . |
| 0046953 | 5/1981 | European Pat. Off. . |
| 0031741 | 7/1981 | European Pat. Off. . |
| 0037231 | 10/1981 | European Pat. Off. . |
| 2470767 | 6/1981 | France . |
| 51455664 | 11/1980 | Japan . |
| 2085880 | 5/1982 | United Kingdom . |

OTHER PUBLICATIONS

Y. Omoto et al., Chemical Abstracts 65, 15304e (1966), abstract of Nippon Kagaku Zasshi 87, 760 (1966).
U. Wolcke et al., Helv. Chim. Acta 53, 11704 (1970).
A. Patchett et al., Nature 288, 280 (1980).
Cushman et al., Biochemistry 16, 5484 (1977).
Cushman et al., Progress in Cardiovascular Diseases, 21, 176, (1978).
Abstract of European Pat. No. 46953, 03/10/1982.

*Primary Examiner*—Paul M. Coughlan, Jr.
*Assistant Examiner*—M. C. Eakin
*Attorney, Agent, or Firm*—Norbert Gruenfeld

[57] ABSTRACT

1-Carboxy-(alkanoyl or aralkanoyl)-indoline-2-carboxylic acids, e.g., those of the formula $$R-\begin{array}{c}\phantom{X}\\\phantom{X}\end{array}\begin{array}{c}CH_2\\|\\CH-COOH\end{array}$$
$$\phantom{XXX}N$$
$$\phantom{XXX}|$$
$$\phantom{XX}CO-CH-(CH_2)_m-CH-COOH$$
$$\phantom{XXXXX}|\phantom{XXXXXXXX}|$$
$$\phantom{XXXX}(CH_2)_p-H\phantom{XX}(CH_2)_q-R'$$

R=H, alkyl, alkoxy, halogeno or $CF_3$;
R'=H or R-phenyl;
m=0 or 1;
p,q=0 to 2;

and derivatives thereof, are antihypertensive and cardioactive agents.

15 Claims, No Drawings

1-CARBOXYALKANOYLINDOLINE-2-CARBOXYLIC ACIDS

CROSS-REFERENCE TO RELATED APPLICATIONS

This is a continuation-in-part of application Ser. No. 235,294, filed Feb. 17, 1981, now U.S. Pat. No. 4,374,847, which is in turn a continuation-in-part of application Ser. No. 200,706 filed Oct. 27, 1980, and now abandoned.

BACKGROUND OF THE INVENTION

1-Alkanoylindoline-2-carboxylic acids and their 5,6-dihydroxy-derivatives, i.e., N-acylated Cyclodopaderivatives, are described in Nippon Kagaku Zasshi 87, 760 (1966) and U.S. Pat. No. 3,796,723 or Helv. Chim. Acta 53, 1701 (1970) respectively, e.g., as synthetical examples of O- and/or N-acylations. Also, 1-carboxyacyl-(azetidine, pyrrolidine or piperidine)-2-carboxylic acids and their functional derivatives are known, e.g., according to U.S. Pat. No. 4,052,511, as possessing antihypertensive activity. Surprisingly it was found that either by introduction of a carboxy group into the former indolines, or by extension of the latter pyrrolidines to the indoline ring-system, superior antihypertensive agents are obtained.

SUMMARY OF THE DISCLOSURE

The present invention concerns and has for its object the provision of new 1-carboxy-(alkanoyl or aralkanoyl)-indoline-2-carboxylic acids, more particularly of those corresponding to Formula I:

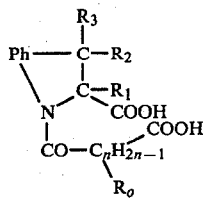

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_0$ is hydrogen or HPh; each of $R_1$, $R_2$ and $R_3$ is hydrogen or lower alkyl; and n is an integer from 1 to 10; the unsubstituted amides and mono- or di-lower alkylamides thereof; lower alkylene amides thereof, wherein the lower alkylene group together with the amide nitrogen forms a 5-, 6- or 7-membered ring, or said lower alkylene amides substituted on the ring by hydroxy-(lower)alkyl or by lower alkanoyloxy-(lower)alkyl; α-(lower)-carboalkoxy- or α-carboxy-substituted lower alkylamides thereof; α-(lower)carboalkoxy- or α-carboxy-substituted aryl-(lower) alkylamides in which aryl represents phenyl or 3-indolyl; (amino or acylamino)-(lower) alkylamides thereof; lower alkyl esters thereof; (amino, mono- or di-lower alkylamino, carboxy or lower carboalkoxy)-substituted lower alkyl esters thereof; aryl-(lower) alkyl esters thereof in which aryl represents phenyl or pyridyl; lower alkanoyloxy-(lower) alkyl esters thereof; phthalidyl esters thereof; (hydroxy, lower alkanoyloxy, or lower alkoxy)-substituted (lower) alkoxymethyl esters; bicycloalkyloxycarbonyl-(lower) alkyl esters thereof having up to 10 carbon atoms in the bicycloalkyl group; or pharmaceutically acceptable salts thereof; as well as of corresponding pharmaceutical compositions and the methods for the preparation and application of said products, which are useful antihypertensive and cardioactive agents.

DESCRIPTION OF THE PREFERRED EMBODIMENTS

Preferred are the compounds of formula I in which Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_0$ is hydrogen or HPh; each of $R_1$, $R_2$ and $R_3$ is hydrogen or lower alkyl; and n is an integer from 1 to 10; the above said amides and esters thereof; and pharmaceutically acceptable alkali metal, alkaline earth metal or ammonium salts of said acids, or acid addition salts of said aminoalkyl esters and amides.

More preferred are those compounds of Formula I, wherein Ph is 1,2-phenylene, unsubstituted or monosubstituted by lower alkyl, lower alkoxy, lower alkylenedioxy, hydroxy, halogeno or trifluoromethyl; $R_0$ is hydrogen or HPh; each of $R_1$, $R_2$ and $R_3$ is hydrogen or methyl; and n is an integer from 2 to 8; and said ester, amide and salt derivatives thereof.

The 1,2-phenylene group Ph and/or the phenyl group HPh, are preferably unsubstituted or monosubstituted, and their substituents are illustrated by the following groups: lower alkyl, e.g., methyl, ethyl, n- or i-propyl or -butyl; lower alkoxy, e.g., methoxy, ethoxy, n- or i-propoxy or -butoxy; lower alkylenedioxy, e.g., methylenedioxy, 1,1- or 1,2-ethylenedioxy; hydroxy; halogeno, e.g., fluoro, chloro or bromo; or trifluoromethyl.

Advantageously the group Ph represents 1,2-phenylene unsubstituted or monosubstituted by chloro, methoxy or methyl. Similarly the group HPh advantageously represents phenyl unsubstituted or monosubstituted by chloro, methoxy or methyl.

Each of $R_1$, $R_2$ and $R_3$ is preferably hydrogen, but also lower alkyl, advantageously methyl, or another of those mentioned previously.

The term "lower", referred to above and hereinafter in connection with organic radicals or compounds respectively, defines such with up to 7, preferably up to 4, and advantageously but one or two carbon atoms.

The alkylene or aralkylene moiety $C_nH_{2n-1}—R_o$ is either straight, or preferably branched, and contains advantageously up to 8 chain-carbon atoms. Thus, it represents for example, in case $R_o=H$, ethylene, 1,2- or 1,3-propylene, 2-methyl-1,2- or -1,3-propylene, 1,2-, 1,3-, 2,3- or 1,4-butylene, 1,2-, 1,3-, 1,4-, 2,4- or 1,5-pentylene; or in case $R_o=$phenyl, ω-phenyl-(1,2-, 1,3- or 2,3- propylene,-butylene or -pentylene, 1,3-, 2,3- or 2,4-butylene, -pentylene or -hexylene, or 3,5-heptylene or -octylene).

Said mono- or bis- functional derivatives of the indoline-2-carboxylic acids of formula I wherein either one or both carboxy groups are esterified or amidized, are preferably unsubstituted amides; N-mono or di-lower alkylamides, e.g. mono-or di-methylamides; N-lower alkyleneamides, e.g. N-butylene, N-pentylene amides in which e.g. butylene or pentylene together with the amide nitrogen forms a pyrrolidine or piperidine ring respectively; substituted lower alkylene amides substituted on e.g. the pyrrolidine or piperidine ring by hydroxy-(lower)alkyl, preferably hydroxymethyl, or by lower alkanoyloxy-(lower)alkyl, preferably acetoxymethyl; α-(lower) carboalkoxy- or carboxy-substituted lower alkylamides, e.g. mono N-(carboethoxymethyl)amides, and mono N-(carboxymethyl)amides; α-(lower) carboalkoxy or carboxy-substituted aryl(lower) alkylamides, e.g. (carboethoxy or carboxy)substituted phenethylamides; amino(lower)alkylamides, e.g. β-aminoethylamides and β-(carbobenzyloxyamino)ethylamides; lower alkyl esters, e.g. the methyl, ethyl, n- or i-propyl or -butyl esters; substituted lower alkyl esters e.g. the ω-amino, ω-mono- or N-dimethylamino, α-carboxy or α-carbethoxy-(ethyl, propyl or butyl) esters; aryl(lower)alkyl esters, e.g. benzyl, (methyl-, methoxy-, chloro-)substituted benzyl, and pyridylmethyl esters; lower alkanoyloxy-(lower)alkyl esters, e.g. pivaloyloxymethyl esters; 3-phthalidyl and (methyl-, methoxy-, chloro-)substituted 3-phthalidyl esters, derived from the corresponding 3-hydroxyphthalides, (hydroxy-, lower alkanoyloxy-, lower alkoxy-) substituted lower alkoxymethyl esters e.g. β-(hydroxy-,acetyloxy-, methoxy-) ethoxymethyl esters; bicycloalkyloxy-carbonyl-(lower) alkyl esters, e.g. those derived from bicyclic monoterpenoid alcohols, such as unsubstituted or lower alkyl substituted bicyclo [2,2,1]heptyloxycarbonyl-(lower)alkyl esters, advantageously bornyloxycarbonylmethyl esters.

Most preferred are the above monofunctional derivatives of the dicarboxylic acids of formula I having a free indoline-2-carboxy group.

Pharmaceutically acceptable salts are preferably metal or ammonium salts of said acids, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris(hydroxymethyl)-aminomethane or benzyl-trimethylammonium hydroxide. Said basic (amino, mono- or di-lower alkylamino)-lower alkyl esters form also acid addition salts, which are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent an object of this invention.

Said esters are preferably, e.g., the straight chain or branched lower alkyl esters unsubstituted or suitably substituted such as the pivaloyloxymethyl, bornyloxycarbonylmethyl, pyridylmethyl, α-carboxyethyl or suitably esterified α-carboxyethyl esters, and the like which are prepared by methods well known to the art and exemplified herein.

Said amides are preferably e.g. simple primary and secondary amides and amides derived from the amino acids or derivatives thereof, such as the amides derived from alanine, phenylalanine and the like.

The compounds of this invention exhibit valuable pharmacological properties, primarily hypotensive, antihypertensive and cardioactive effects, inter alia due to their angiotensin converting enzyme inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starchy suspensions or aqueous solutions respectively. The applied dosage may range between about 0.01 and 100 mg/kg/day, preferably between about 0.1 and 50 mg/kg/day advantageously between about 0.1 and 25 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, representative members of the compounds of this invention, illustrated by the Examples herein, are very effective in hypertensive rats and dogs at p.o.-doses as low or lower than 50 mg/kg/day.

Illustrative of the invention, 1-(4-carboethoxy-2R,4R-dimethylbutanoyl)-indoline-2S-carboxylic acid and 1-(4-carboethoxy-2R-methyl-4R-phenethyl-butanoyl)-indoline-2S-carboxylic acid significantly lower blood pressure and decrease heart rate in the spontaneous hypertensive rat at a dose of 30 and 10 mg/Kg p.o. respectively.

The compounds of the invention also exhibit an inhibitory effect against the angiotensin I pressure response of normotensive rats. The enzyme renin normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor responses to 3 challenges of 0.33 μg/kg of angiotensin I i.v., in 5 minute intervals, are obtained. Such pressure responses are again obtained 5, 10, 15, 30 and 60 minutes after either i.v., or p.o. administration (stomach tube) of the compounds to be tested, and compared with the initial responses. Any observed decrease of said pressor response is an indication of angiotensin I converting enzyme inhibition, ranging up to 80% after 10 mg/kg i.v., or 50 mg/kg p.o or lower doses, which decrease may be sustained up to 60 minutes.

Illustrative of the invention, 1-(4-carboethoxy-2R,4R-dimethylbutanoyl)indoline-2S-carboxylic acid inhibits the pressor response following angiotensin I challenge by about 50% in the rat at dose as low as 4 mg/Kg p.o. or 0.3 mg/Kg i.v.

Further illustrative of the invention, 1-[4-(pivaloyloxymethoxycarbonyl)-2R,4R-dimethyl-butanoyl]-indoline-2S-carboxylic acid and 1-[4-l-bornyloxycarbonylmethoxycarbonyl)-2R,4R-dimethylbutanoyl]-indoline-2S-carboxylic acid inhibit the pressor response following angiotensin I challenge in the dog at an oral dose of 10 mg/Kg.

The in vitro inhibition of the angiotensin-converting enzyme by the compounds of this invention can be demonstrated analogous to Biochim. Biophys. Acta 293, 451 (1973). According to this method said compounds are dissolved at about 1 mM concentrations in phosphate buffer, externally cooled with ice. To these solutions various μl amounts of 1 mM of histidyl-leucine in phosphate buffer are added, followed by 100 μl of 5 mM hippuryl-histidyl-leucine in phosphate buffer and 50 μl of the angiotensin-converting enzyme, which is freshly prepared from lungs of adult male rabbits in Tris buffer, containing potassium and magnesium chloride, as well as sucrose. Said solutions are incubated at 37° for 30 minutes and combined with 0.75 ml of 0.6 N aqueous sodium hydroxide to stop further reaction. Then 100 μl of o-phthalaldehyde are added at room temperature, and 10 minutes later 100 μl of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the $IC_{50}$, i.e., the drug concentration which gives half the activity of the control sample containing no drug. Again, said representative members of the compounds of this invention are very effective in this in vitro test system, down to $IC_{50}$ values as low or lower than 10 nM.

Illustrative of the invention 1-(4-carboxybutanoyl)-indoline-2S-carboxylic acid, 1-(4-carboxy-2R-methylbutanoyl)-indoline-2S-carboxylic acid, 1-(4-carboxy-2R,4R-dimethylbutanoyl)-indoline-2S-carboxylic acid, 1-(4-carboxy-2R-methyl-4R-phenethylbutanoyl)-indoline-2S-carboxylic acid show an $IC_{50}$ of about 300, 40, 30 and 5 nM respectively.

Accordingly, the compounds of this invention are valuable antihypertensive agents, especially useful for ameliorating hypertension (regardless of etiology) and/or heart-conditions, such as congestive heart failure, and/or other edemic or ascitic diseases, e.g. hepatic cirrhosis. They are also useful intermediates in the preparation of other valuable products, especially of corresponding pharmaceutical compositions.

Especially valuable compounds of this invention are those of Formula II

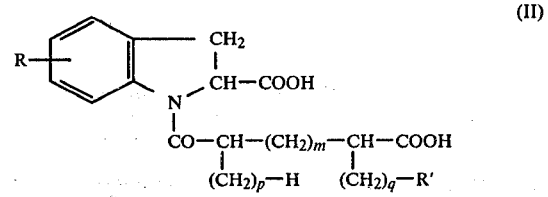

more specifically the indoline-2S-chiral epimers thereof, wherein R is hydrogen, alkyl or alkoxy with up to 4 carbon atoms, halogeno or trifluoromethyl; m is the integer 0 or 1; each of p and q is an integer from 0 to 2; and R' is hydrogen or R-phenyl in which R-phenyl represents phenyl unsubstituted or monosubstituted by alkyl or alkoxy with up to 4 carbon atoms, halogeno or trifluoromethyl; the mono- or bis-amide, a mono- or bis-lower (alkyl or ω-aminoalkyl) ester; a mono α-(lower)carbalkoxy- or α-carboxy-substituted lower alkylamide; a mono α-(lower) carbalkoxy- or α-carboxy-substituted aryl-(lower) alkylamide in which aryl represents phenyl; a mono carboxy- or lower carbalkoxy-substituted lower alkyl ester; a mono aryl(lower)alkyl ester in which aryl represents phenyl or pyridyl; a mono bicycloalkyloxycarbonyl(lower)alkyl ester in which bicycloalkyl represents bornyl; a mono lower alkanoyloxy (lower) alkyl ester; or a pharmaceutically acceptable alkali metal or ammonium salt of any said acid, or acid addition salt of any said aminoalkyl ester.

The side chain

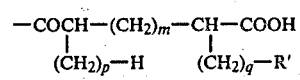

in the compounds of formula II can exist in two distinct diasteromeric forms (called "erythro" and "threo" herein) depending on the relative orientation of the $(CH_2)_p$—H and the $(CH_2)_q$—R' substituents on the chain (when neither of said groupings represents hydrogen).

Preferred are the compounds of formula II having the said side chain in the "threo" form, advantageously with both carbon atoms bearing said substituents being in the (R)-configuration. Most preferred are the compounds of formula IIa, given hereinafter, wherein the 2-indoline carbon atom bearing the COOH group is in the (S)-configuration, and either or both of the carbon atoms bearing the $(CH_2)_p$—H and $(CH_2)_q$—R' substituents are in the (R)-configuration (whenever said groups do not represent hydrogen).

The most preferred compounds of this invention are those of Formula II, wherein R is hydrogen, methyl, methoxy, fluoro, chloro or trifluoromethyl, advantageously in the 5-position, each of m and p is the integer 1, q is the integer 1 or 2, and R' is hydrogen or phenyl, or said functional acid and amino derivatives listed above.

The compounds of this invention are prepared according to conventional methods, advantageously by:

(1) condensing a compound of Formula III

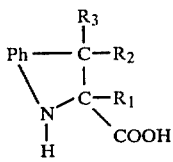

or said acid or amino derivatives thereof, with a reactive functional derivative of a compound of Formula IV

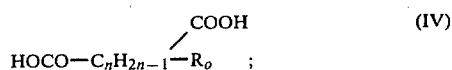

or (2) hydrolysing or alcoholyzing a compound of Formula V

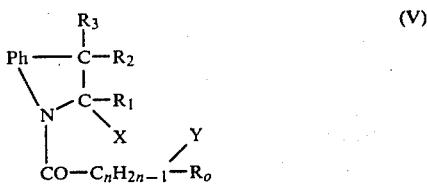

wherein at least one of X and Y is cyano, and the other is said free, amidized or esterified carboxy group; or (3) hydrogenating in a compound of Formula VI

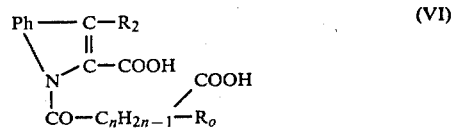

or said acid or amino derivatives thereof, the indole moiety to the indoline moiety; and, if desired, converting any resulting compound into another compound of this invention.

Reactive functional derivatives of compounds IV are preferably ester-halides, simple or mixed anhydrides, such as the lower alkyl half esters of said acid chlorides, the cyclic anhydride, or mixed acetic or cyanoacetic anhydrides. Said condensation of compounds III and IV occurs either spontaneously, or in the presence of condensing agents, such as organic or inorganic bases, e.g. said salt-forming amines or alkali metal carbonates, or disubstituted carbodiimides.

Said hydrolysis of the nitriles V to the corresponding acids or amides is advantageously carried out with inorganic acids, such as hydrohalic or sulfuric acids, in known manner; and said alcoholysis is analogously performed in the presence of both said acids and the corresponding unsubstituted or substituted lower alkanols.

Finally, said hydrogenation of the indoles VI to the indolines I is also performed according to conventional hydrogenations of 1-acyl-indoles, for example, with catalytically activated or nascent hydrogen, e.g. hydrogen in the presence of platinum, palladium, rhodium or nickel catalysts, or hydrogen generated electrolytically, or by the action of metals on acids or alcohols. Also reducing agents may be used, such as simple or complex light metal hydrides, e.g. boranes, or advantageously alkali metal borohydrides or cyanoborohydrides. Preferred is the asymmetric hydrogenation to the indoline-2S-carboxylic acids, or said derivatives thereof, with chiral catalysts, as, for example, prepared from a rhodium salt with (R)-1,2-bis-(diphenylphosphino)propane on (R)-1,2-bis(o-anisylphenylphosphino )-ethane and 1,5-cyclooctadiene.

The compounds of the invention so obtained, can be converted into each other according to conventional methods. Thus, for example, resulting amides or esters may be further hydrolyzed or alcoholyzed (transesterified) according to process 2), or with aqueous alkalies, such as alkali metal carbonates or hydroxides, respectively. Resulting free acids may be esterified with e.g. said unsubstituted or substituted lower alkanols, alkyl halides, or diazoalkanes, or converted into said metal, ammonium or acid addition salts in conventional manner.

Thus, for example, any resulting free acid or base can be converted into a corresponding metal, ammonium or acid addition salt respectively, by reacting it with an equivalent amount of the corresponding base, basic salt, acid or ion exchange preparation, e.g. said acids with alkali or ammonium hydroxides or carbonates, or said aminoalkyl esters with said inorganic or organic acids respectively. Any resulting salt may also be converted into the free compounds, by liberating the latter with stronger acids or bases respectively. In view of the close relationship between the free compounds, and the salts thereof, whenever a compound of the invention, or intermediate thereof, is referred to in this context, a corresponding salt is also intended, provided such is possible or appropriate under the circumstances.

The starting material of Formulae III and IV is known, or, if new, may be prepared according to conventional methods, e.g., those illustrated by the examples herein. Compounds of Formula V, are also obtained according to conventional methods, e.g., by condensing the corresponding nitriles of Formulae III and/or IV according to said process 1.

In case mixtures of geometrical or optical isomers of the above compounds of Formulae I to V are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrates, mandelates, camphorsulfonates, or 1-naphthyl-1-ethylisocyanates), or of d- or l-(α-methylbenzylammonium, cinchonidine, cinchonine, quinine, quinidine, ephedrine, dehydroabiethylamine, brucine or strychnine)-salts. The preferred starting material of Formula III is the 2-S-optical isomer (epimer) thereof.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably at the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g., those of Formula II, and being the following chiral isomers:

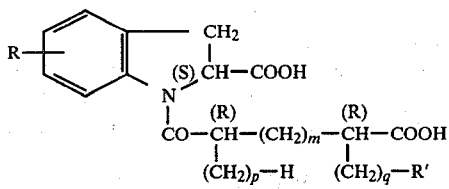

The indolines of the invention may be converted by reduction to the perhydro derivatives thereof, e.g. to the compounds of formula VII,

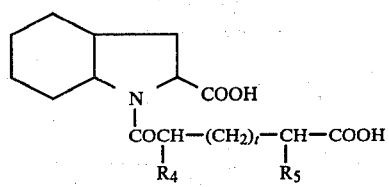

preferably the cis fused perhydroindole-2S-epimers, wherein $R_4$ represents hydrogen or lower alkyl of up to 4 carbon atoms; $R_5$ represents lower alkyl of up to 4 carbon atoms; or $R_5$ represents lower alkyl of up to 4 carbon atoms substituted by aryl in which aryl represents phenyl or phenyl mono-substituted by lower alkyl, lower alkoxy or halogen; t represents 0 or 1; the mono or bis lower alkyl esters thereof; and pharmaceutically acceptable salts thereof.

Also included are other functional derivatives, especially pro-drug functional derivatives, cited above for the corresponding indolines of the invention.

The perhydroindole (octahydroindole) derivatives, e.g. those of formula VII are also useful as antihypertensive, cardioactive and angiotensin-converting enzyme inhibitors. Preferred are the compounds wherein $R_5$ represents methyl or phenethyl and t represents 1. Further preferred are the compounds wherein the carbon atoms bearing $R_4$ and $R_5$ are in the (R)-configuration.

The reduction of the indoline derivatives of the invention to said perhydroindoles is advantageously carried by hydrogenation in the presence of a hydrogenation catalyst, e.g. rhodium, in an inert solvent such as ethanol, at atmospheric or superatmospheric pressure, and preferably at a temperature range of 20° to 50°.

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, or effervescent mixtures and/or (e) absorbents, colorants, flavors and sweeteners. Injectable compositions are preferably aqueous isotonic solutions or suspensions; and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances, e.g. other antihypertensive agents and/or diuretics. Said compositions are prepared according to conventional mixing, granulating or coating methods respectively, and contain about 0.1 to 75%, preferably about 1 to 50% of the active ingredient. A unit dosage for a mammal of about 50-70 kg weight may contain between about 5 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the suspension of 5.0 g of indoline-2S-carboxylic acid ethyl ester hydrochloride, 9.1 g of powdered potassium carbonate and 45 ml of methylene chloride, 3.61 g of methyl glutaroyl chloride in 5 ml of methylene chloride are added while stirring at room temperature. The mixture is stirred overnight at room temperature, cooled with ice, and 100 ml of water are added. The organic layer is separated, washed with N-hydrochloric acid and water, dried and evaporated, to yield the 1-(4-carbomethoxybutanoyl)-indoline-2S-carboxylic acid ethyl ester melting at 88°-90°.

The starting material is prepared as follows: 120 g of 1-acetylindoline-2-carboxylic acid [Nippon Kagaku Zasshi 87, 760 (1966)] and 172 g of l-cinchonidine are dissolved in 1,200 ml of hot ethanol. The solution is allowed to stand at room temperature overnight and then at 0° for 4 days. The white crystalline salt is filtered off and discarded. The filtrate is evaporated, 1,000 ml of water are added and the solution is adjusted to pH =1 with concentrated hydrochloric acid. After 15 minutes the product is collected by filtration and washed thrice with 250 ml of 2N aqueous hydrochloric acid, twice with 500 ml of water and twice with 100 ml of ethanol, to give the 1-acetylindoline-2S-carboxylic acid melting at 214°-215°; $[\alpha]_D = -133.3°$ (c=1.165 in ethanol).

The suspension of 37.5 g thereof in 380 ml of 2N aqueous hydrochloric acid is deoxygenated by bubbling nitrogen through it for 5 minutes, followed by refluxing for 2 hours. It is cooled to room temperature, filtered through infusorial earth, the filtrate evaporated and the residue crysallized from diethyl ether-isopropanol, to yield the indoline-2S-carboxylic acid hydrochloride melting at 133° (dec.); $[\alpha]_D = -70.4°$ (c=1 in ethanol).

The solution of 34 g thereof in 350 ml of ethanol is saturated with dry hydrogen chloride without external cooling. The mixture is stirred for 2 hours at room temperature and the solvent removed until crystallization begins. The concentrate is poured into 400 ml of diethyl ether, cooled at 0° for 1 hour and filtered, to yield the indoline-2S-carboxylic acid ethyl ester hydrochloride melting at 179°-181°; $[\alpha]_D = -63°$ (c=1.385 in ethanol).

EXAMPLE 2

To the suspension of 5.0 g of 1-(4-carbomethoxybutanoyl)-indoline-2S-carboxylic acid ethyl ester in 47 ml of methanol is added 47 ml of N aqueous sodium hydroxide and the mixture is stirred at room temperature for 4 hours. It is concentrated at room temperature and reduced pressure, the aqueous solution acidified with concentrated hydrochloric acid while cooling, the resulting precipitate collected, washed with water and dried, to yield the 1-(4-carboxybutanoyl)-indoline-2S-carboxylic acid melting at 175°-177°; $[\alpha]_D = -97.8°$ (c=1.0 in ethanol).

EXAMPLE 3

To the solution of 11 g of indoline-2S-carboxylic acid hydrochloride in 75 ml of pyridine, 8.25 g of 4-carbomethoxy-2-methylbutanoyl chloride are added and the mixture is stirred at room temperature overnight. The pyridine is distilled off at room temperature and reduced pressure, the residue is cooled, acidified with 3N hydrochloric acid and extracted with methylene chloride. The extract is evaporated, the residue dissolved in diethyl ether and the solution combined with that of 10 ml of dicyclohexylamine in 25 ml of hexane. The precipitate is collected, washed with hot ethyl acetate and suspended in acetone overnight, to yield the dicyclohexylammonium 1-(4-carbomethoxy-2-methylbutanoyl)-indoline-2S-carboxylate, melting at 203°-205°; the corresponding free acid melts at 97°-99°.

The first starting material is described as intermediate in Example 1, and the second may be prepared as follows:

9.64 g of oxalyl chloride are added to the solution of 6.1 g of 4-carbomethoxy-2-methylbutanoic acid (US-Patent 4,052,511) in 50 ml of methylene chloride. The mixture is refluxed for two hours and evaporated, to yield the 4-carbomethoxy-2-methylbutanoyl chloride, which is used as such without further purification.

EXAMPLE 4

The solution of 2.03 g of indoline-2S-carboxylic acid ethyl ester and 2.5 g of 2-(2-phenethyl)-glutaric acid anhydride in 75 ml of toluene, is heated to 70° overnight under nitrogen. It is evaporated, the residue dissolved in diethyl ether, the solution washed with N hydrochloric acid and extracted with saturated aqueous sodium bicarbonate. The extract is cooled, acidified with hydrochloric acid and re-extracted with methylene chloride. The organic extract is evaporated, the residue dissolved in diethyl ether and the solution combined with that of 1.2 ml of dicyclohexylamine in 25 ml of hexane. The resulting precipitate is filtered off and washed with hexane, to yield the dicyclohexylammonium 1-[4-carboxy4-(2-phenethyl)-butanoyl]-indoline-2S-carboxylic acid ethyl ester, melting at 132°-134°. It may be re-converted to the free acid with N hydrochloric acid.

The starting material is prepared as follows: 29.8 g of indoline-2S-carboxylic acid ethyl ester hydrochloride are partitioned between 300 ml of saturated aqueous sodium bicarbonate and 100 ml of methylene chloride. The aqueous layer is extracted twice with additional 200 ml of methylene chloride, the combined organic layers washed with saturated aqueous sodium chloride and evaporated, to yield the indoline-2S-carboxylic acid ethyl ester as an oil, showing the major IR-band at 1730 $cm^{-1}$.

The solution of 12 g of 2-(2-phenyethyl)glutaric acid [J. Chem. Soc. 1950, 1683] in 75 ml of acetic acid anhydride is refluxed for 4 hours and evaporated. The residue is crystallized from diethyl ether, to yield the corresponding anhydride melting at 78°-80°.

EXAMPLE 5

The solution of 2.4 g of 1-[4-carboxy-4-(2-phenethyl)-butanoyl]-indoline-2S-carboxylic acid ethyl ester in 17.6 ml of methanol and 17.6 ml of N aqueous sodium hydroxide is stirred at room temperature for 2.5 hours. It is concentrated at room temperature under reduced pressure, the aqueous solution filtered, acidified with hydrochloric acid and extracted with methylene chloride. The extract is evaporated and the residue crystallized from petroleum ether, to yield the 1-[4-carboxy-4-(2-phenethyl)-butanoyl]indoline-2S-carboxylic acid melting at 136°-138°.

EXAMPLE 6

According to the methods illustrated by the previous examples, the following 1-(carboxyalkanoyl or -aralkanoyl)-indoline-2S-carboxylic acids of Formula I, with Ph=1,2-phenylene and $R_1=R_2=R_3=H$, as well as said derivatives thereof, are prepared:

| No | $C_nH_{2n-1}R_o-$ | $C_nH_{2n-1}R_o-$ COOH deriv. | Indoline-2-COOH der. | m.p. °C., or NMR |
|---|---|---|---|---|
| 1 | CH—CH$_2$<br>\|<br>CH$_3$ | — | — | 122-124°, 83-85° for hemihydrate |
| 2 | (CH$_2$)$_2$—CH<br>\|<br>CH$_3$ | — | ethyl ester | 104-106° |
| 3 | " | — | — | 172-174° |
| 4 | CH—(CH$_2$)$_2$<br>\|<br>CH$_3$ | methyl ester | ethyl ester | 4.25, 3.65 1.30 ppm |
| 5 | " | — | — | 72-74° |
| 6 | CH$_2$—CH—CH$_2$<br>\|<br>CH$_3$ | — | ethyl ester | 111-113° |
| 7 | " | — | — | 125-127° |
| 8 | CH—CH$_2$—CH<br>\|   \|<br>CH$_3$  CH$_3$<br>(erythro) | — | ethyl ester D | 132-134° |
| 9 | CH—CH$_2$—CH<br>\|   \|<br>CH$_3$  CH$_3$<br>(erythro) | — | — | 58-60° |
| 10 | CH—CH$_2$—CH<br>\|   \|<br>CH$_3$  CH$_3$<br>(threo) | — | — | 70-72° |

D = dicyclohexylammonium salt

Similarly prepared are the following:

| No. | $C_nH_{2n-1}R_o$ | $C_nH_{2n-1}R_o-$COOH deriv. | Indoline-2-COOH der. |
|---|---|---|---|
| 11 | CH—CH$_2$—CH<br>\|        \|<br>CH$_3$  (CH$_2$)$_2$)—C$_6$H$_5$<br>(erythro) | — | — |
| 12 | CH—CH$_2$—CH<br>\|        \|<br>CH$_3$  (CH$_2$)$_2$)—C$_6$H$_5$<br>(threo) | — | — |

The starting materials for said compounds 1, 2, 4, 6, 11 and 12 are the 3-carbomethoxy-2-methylpropanoyl chloride, 2-methylglutaric anhydride, 4-carbomethoxy-2-methylbutanoyl chloride, 3-methylglutaric anhydride and the erythro or threo 4-carbomethoxy-4-(2-phenethyl)-2-methylbutanoyl chloride respectively. That of compound 8 and 9 may be prepared as follows: The solution of 6.0 of meso-2,4-dimethylglutaric acid anhydride [J. Am. Chem. Soc. 77, 1862 (1955)] in 4 ml of methanol is refluxed for one hour and evaporated, to yield the erythro 4-carbomethoxy-2,4-dimethylbutanoic acid. It is converted into the acid chloride by refluxing it with 10.9 g of oxalyl chloride in 50 ml of methylene chloride for 2 hours, and evaporating said mixture.

The corresponding threo-isomer is analogously obtained from the racemic anhydride.

EXAMPLE 7

The solution of 1 g of 1-(4-carbomethoxy-2-methylbutanoyl)-indoline-2S-carboxylic acid (Example 3) in 10 ml of methanol is saturated with ammonia at 0° and stored in a pressure bottle at room temperature for 4 days. It is evaporated, the residue taken up in water, the mixture acidified with 2N hydrochloric acid at 0° and the addition of a few drops of methylene chloride initiates crystallization. The mixture is filtered and the residue triturated with diethyl ether, to yield the 1-(4-carbamoyl-2-methylbutanoyl)-indoline-2S-carboxylic acid melting at 192°–194°.

EXAMPLE 8

(a) To a solution of 1.43 g of indoline-2S-carboxylic acid hydrochloride in 15 ml pyridine at 0° C. is added 1.35 g of 4-carboethoxy-2R,4R-dimethylbutanoyl chloride. The reaction mixture is stirred at room temperature for 3 hours and evaporated under vacuum. The residue is treated with 20 ml of 3N hydrochloric acid and extracted three times with 10 ml of methylene chloride and the extract is evaporated to dryness. The 1-(4-carboethoxy-2R,4R-dimethylbutanoyl)indoline-2S-carboxylic acid obtained is dissolved in 75 ml of ether and treated with 2.2 ml dicyclohexylamine to yield the crystalline dicyclohexylammonium salt. This is slurried in a mixture of 40 ml of ethyl acetate and 45 ml of 5% aqueous potassium bisulfate solution for 1 hour. The ethyl acetate layer is separated, washed with water, dried over sodium sulfate, and evaporated to dryness. Crystallization form hexane yields 1-(4-carboethoxy-2R,4R-dimethylbutanoyl)indoline-2S-carboxylic acid, melting at 125°–7°, $[\alpha]_D = -159°$ (C=0.2 Sin ethanol).

(b) By using 4-carboethoxy-2R-methylbutanoyl chloride instead of the 4-carboethoxy-2R,4R-dimethylbutanoyl chloride as described above, one obtains 1-(4-carboethoxy-2R-methylbutanoyl)indoline-2S-carboxylic acid, melting at 133°–135° C., $[\alpha]_D = -120.5°$ (C=0.2 in ethanol).

(c) Similarly prepared is 1-(4-carboethoxy-2R-isopropylbutanoyl)indoline2S-carboxylic acid.

(d) Prepared similarly are 1-(4-carboethoxy-2R,4R-dimethyl-butanoyl)indoline-2S-carboxylic acids wherein the 5-position of the indoline nucleus is substituted by either methoxy, chloro or methyl.

The starting materials are prepared as follows:
A solution of 3.7 g of 2R-methylglutaric acid [J. Am. Chem. Soc. 77, 3383 (1955)] in 10 ml of acetyl chloride is stirred at 50° for 2 hours. The reaction mixture is evaporated to dryness to yield the 2R-methylglutaric anhydride, melting at 50°–2° $[\alpha]_D = +43.8°$ (C=1.0 in chloroform). 2R,4R-dimethylglutaric anhydride, melting at 43°–5°, $[\alpha]_D = +56.5°$ (C=1.0, chloroform) is prepared in identical fashion from 2R, 4R-dimethylglutaric acid [Arkiv Kemi Mineral Geol. B14, 1 (1940), $[\alpha]_D = -35.5°$ (C=2.0 in ethanol].

Similarly prepared is the 2R-isopropylglutaric anhydride from the corresponding 2R-isopropylglutaric acid [Arkiv Kemi Mineral Geol. B23, 1 (1946)].

A solution of 1.7 g of 2R,4R-dimethylglutaric anhydride in 40 ml of absolute ethanol is heated under reflux overnight and evaporated to dryness to yield 4-carboethoxy-2R,4R-dimethylbutanoic acid as an oil, $[\alpha]_D = -49.4°$ (c=1.0 in ethanol).

A solution of 2.9 g of 2R-methylglutaric anhydride in 10 ml of ethanol is refluxed for 3 hours and evaporated to dryness. A solution of the oil in 25 ml of ether is treated with 5.0 ml of dicyclohexylamine in 25 ml of hexane to yield the 4-carboethoxy-2R-methylbutanoic acid as the dicyclohexylammonium salt, m.p. 98°–100°. Conversion to the free acid with 1N hydrochloric acid and extraction with ethyl acetate gives 4-carboethoxy-2R-methylbutanoic acid as an oil, $[\alpha]_D = -20.9°$ (c=1.0 in chloroform).

A solution of 1.27 g of 4-carboethoxy-2R,4R-dimethylbutanoic acid in 15 ml of methylene chloride is treated with 1.7 g of oxalyl chloride, heated under reflux for 3 hours and evaporated to dryness to yield 4-carboethoxy-2R,4R-dimethylbutanoyl chloride, NMR peaks at 1.8,2.5, 2.8,4.1 ppm. Similarly prepared are the 4-carboethoxy-2R-methylbutanoyl chloride (NMR peaks at 2.0,2.4, 4.3 ppm) and the 4-carboethoxy-2R-isopropylbutanoyl chloride.

5-methoxyindoline-2-carboxylic acid, 5-chloro-indoline-2-carboxylic acid, and 5-methylindoline-2-carboxylic acid can be prepared from the corresponding substituted indole-2-carboxylic acid according to the method described for Example 1.

EXAMPLE 9

(a) To a solution of 2.63 g of ethyl indoline-2S-carboxylate in 40 ml of methylene chloride containing 4.8 g of anhydrous potassium carbonate is added 2.39 g of 4-carboethoxy-2R,4R-dimethylbutanoyl chloride. The reaction is stirred overnight at room temperature and then extracted with 20 ml of water. The organic layer is washed with 15 ml of 1N hydrochloric acid and 15 ml of water, dried (Na$_2$SO$_4$) and evaporated to give ethyl 1-(4-carboethoxy-2R,4R-dimethylbutanoyl)-indoline-2S-carboxylate as an oil having $[\alpha]_D = -130.10$ (c=1.0 in ethanol).

(b) Similarly prepared is ethyl 1-(4-carboethoxy-2R-methylbutanoyl]-indoline-2S-carboxylate as an oil having NMR peaks at 1.2, 4.1 to 4.3, 4.9, 6.7 and 7.2 ppm, using 4-carboethoxy-2R-methylbutanoyl chloride as the acylating reagent.

EXAMPLE 10

To a solution of 3.2 g of ethyl indoline-2S-carboxylate hydrochloride and 1.47 g of triethylamine in 60 ml of methylene chloride is added 2.34 g of 4-carboethoxy-2R-methylbutanoic acid followed by 2.97 g of 1-(3-dimethylaminopropyl)-3-ethylcarbodiimide hydrochloride. The reaction is stirred at room temperature for 3 days and poured into water. The organic layer is separated and washed successively with 30 ml of 1N hydrochloric acid, 30 ml of water and 30 ml of 10% aqueous sodium bicarbonate solution. The organic layer is dried over sodium sulfate and evaporated to dryness to yield ethyl 1-(4-carboethoxy-2R-methylbutanoyl)indoline-2S-carboxylate identical to the compound of example 9b).

EXAMPLE 11

A solution of 0.45 g of ethyl indoline-2S-carboxylate and 0.30 g of 2R,4R-dimethylglutaric anhydride in 10 ml of toluene is stirred at 70° for 18 hours. The reaction is cooled to room temperature, washed twice with 5 ml of 1N hydrochloric acid and extracted twice with 10 ml of 5% sodium bicarbonate. The combined bicarbonate portions are acidified with 4.0 ml of 12N hydrochloric acid and extracted three times with 10 ml of methylene chloride. The combined methylene chloride portions are dried over $Na_2SO_4$ and evaporated to give ethyl 1-(4-carboxy-2R,4R-dimethyl-butanoyl)-indoline-2S-carboxylate as an oil having NMR peaks at 1.0 to 1.3, 4.15, 5.10, 7.2 and 8.4 ppm.

EXAMPLE 12

(a) To a solution of 3.4 g of ethyl 1-(4-carboethoxy-2R, 4R-dimethylbutanoyl)-indoline-2S-carboxylate in 30 ml of methanol is added 28.2 ml of 1N aqueous sodium hydroxide solution. The reaction mixture is stirred at room temperature for 4 hours, evaporated to remove methanol and acidified with 3.5 ml of cencentrated hydrochloric acid. The mixture is extracted four times with 10 ml of methylene chloride. The combined extract is dried over sodium sulfate and evaporated to dryness and the residue is recrystallized from ether-petroleum ether to give 1-(4-carboxy-2R,4R-dimethylbutanoyl)-indoline-2S-carboxylic acid melting at 132°-134°, $[\alpha]_D = -144°$ (c=1.0 in ethanol).

Similar hydrolysis of 0.46 g of ethyl 1-(4-carboxy-2R,4R-dimethylbutanoyl)-indoline-2S-carboxylate (example 10) and crystallization of the product from water yields the 1-(4-carboxy-2R,4R-dimethylbutanoyl)indoline-2S-carboxylic acid hydrate having a melting point of 93°-95°, $[\alpha]_D = -142.8°$ (c=1.0 in ethanol).

(b) Similarly, hydrolysis of ethyl 1-(4-carboethoxy-2R-methylbutanoyl)indoline-2S-carboxylate yields 1-(4-carboxy-2R-methylbutanoyl)-indoline-2S-carboxylic acid, crystallized from ether and melting at 147°-9°, $[\alpha]_D = -125°$ (c=0.2 in ethanol). Similarly, hydrolysis of 1-(4-carboethoxy-2R-methylbutanoyl)-indoline-2S-carboxylic acid yields the diacid identical to the 1-(4-carboxy-2R-methylbutanoyl)-indoline-2S-carboxylic acid isolated above.

EXAMPLE 13

A solution of 90 mg of indoline-2-S-carboxylic acid hydrochloride is treated with 92 mg of 4-carboethoxy-2R-methyl-4R-phenethylbutanoyl chloride in pyridine by the analogous process described in detail for Example 8 to yield 1-(4-carboethoxy-2R-methyl-4R-phenethylbutanoyl)indoline-2S-carboxylic acid as the dicyclohexylamine salt melting at 146°-149°.

The starting material is prepared in part according to the general process described in Tetrahedron Letters 1980, 4233-6, as follows:

Aqueous sodium hydroxide (1N, 25 ml) is added to a solution of 2.0 g of L-prolinol (U.S. Pat. No. 3,935,280) in 50 ml of $CH_2Cl_2$. After cooling the reaction mixture to 0° C., 4.0 g of 4-phenylbutyric acid chloride is added and the reaction is stirred vigorously for 4 hours at 0° C., followed by 1 hour at room temperature. The reaction is diluted with an equal volume of $CH_2Cl_2$ and the layers separated. The organic phase is washed with 30 ml of water and dried over $Na_2SO_4/K_2CO_3$. The solvent is evaporated to yield 4.4 g of N-(4-phenylbutanoyl)-L-prolinol having IR peaks at 3280 and 1605 $cm^{-1}$, $[\alpha]_D^{25} = -40.3°$ (methanol). 20.5 g of N-methyl-N,N'-dicyclohexylcarbodiimidium iodide (Angew. Chem., Int. Ed. 11, 229 (1972) is added to a solution of 5.3 of R-(−)-3-benzyloxy-2-methylpropanol (Helv. Chim. Acta 60, 925 (1977) in 200 ml dry tetrahydrofuran under nitrogen and the reaction is stirred at room temperature for 14 hours. The solvent is evaporated and 20 ml of ether and 5 ml of pentane are added. The resulting yellow solid is collected and the mother liquors are chromatographed on 200 g of silica gel with pentane to yield 6.68 g of the S(+)-3-benzyloxy-2-methylpropyl iodide having Rf=0.60 (9:1 of pentane: ether/$Si°_2$), $[\alpha]_D^{25} = +11.1°$ (MeOH). N-(4-phenylbutanoyl)L-prolinol is dissolved in 2 ml of dry tetrahydrofuran and added dropwise to a solution of lithium diisopropylamide (15.6 m moles) in 50 ml of tetrahydrofuran at 0° C. under nitrogen. After 30 minutes at 0° C., 2.03 g of S-(+)-3-benzyloxy-2-methylpropyl iodide is added dropwise in 2 ml of dry tetrahydrofuran. The reaction is stirred at 0° C. for 5 hours, at −15° C. for 15 hours and quenched at 0° C. with excess saturated ammonium chloride solution. The reaction mixture is diluted with 30 ml of ether. The layers are separated and the organic phase is washed with 16 ml of 1N HCl, 15 ml of brine, 15 ml of saturated sodium bicarbonate and dried over sodium sulfate. Evaporation of solvent yields 3.6 g of an oil which is filtered through 60 g of silica gel with ethyl acetate to yield 2.3 g of N-(R,R-5-benzyloxy-4-methyl-2-phenethylpentanoyl) L-prolinol having Rf 0.51 (EtoAc/$SiO_2$).

A solution of 2.0 g of N-(R,R-5-benzyloxy-4-methyl-2-phenethylpentanoyl) L-prolinol in 50 ml of 1N ethanolic hydrochloric acid is refluxed under nitrogen for 15 hours. The solvent is evaporated and the residue is chromatographed on 60 g of silica gel with pentane: ether (2:1) to yield 0.65 g of ethyl R,R-5-benzyloxy-4-methyl-2-phenethylpentaoate having Rf 0.37 (9:1 of pentane: ether/$SiO_2$), $[\alpha]_D^{25} + 2.85$ (EtOH).

A solution of 0.6 g of ethyl R,R-5-benzyloxy-4-methyl-2-phenethylpentanoate in 50 ml of anhydrous ethanol is hydrogenated at 40 psi for 3 hours at room temperature with 0.5 g of 5% palladium on charcoal catalyst. The catalyst is then removed by filtering through celite and the solvent is evaporated to yield 0.41 g of ethyl R,R-5-hydroxy-4-methyl-2-phenethylpentanoate having Rf=0.36 (1:1 of pentane-ether).

Ethyl R,R-5-hydroxy-4-methyl-2-phenethylpentanoate (0.35 g) is dissolved in 15 ml of dry dimethylformamide at room temperature under nitrogen. Pyridinium dichromate (2.5 g) is added and the reaction mixture is stirred for 15 hours at room temperature before being poured into 150 ml of water. The aqueous solution is extracted with ether (4×40 ml). The ethereal extracts are washed with 30 ml of water and the three times with 20 ml of a 1:1 solution of sodium bicarbonate: potassium carbonate (pH=10.5). The basic wash is acidified to pH=2 with concentrated sulfuric acid, while keeping the temperature between 5 and 10° C., and extracted with ether (4×20 ml). The ethereal extracts are washed with 20 ml of brine and dried over $Na_2SO_4/MgSo_4$. Evaporation of the solvent yields 0.28 g of 4-carboethoxy-2R-methyl-4R-(phenethyl)butanoic acid, having Rf=0.50 (99:1:100 of ether:AcOH:hexane),- $[\alpha]_D^{25}$ −4.91° (EtOH)

Treatment of 4-carboethoxy-2R-methyl-4R-(phenethyl)butanoic acid with oxalyl chloride in methylene chloride yields 4-carboethoxy-2R-methyl-4R-phenethyl-butanoyl chloride.

EXAMPLE 14

According to the process described for example 10, 79 mg of ethyl indoline-2S-carboxylate hydrochloride is reacted with 96.5 mg of 4-carboethoxy-2R-methyl-4R-(phenethyl)butanoic acid (See example 13) in the presence of 0.05 ml of triethylamine and 66.5 mg of 1-(3-dimethylaminopropyl)-3-ethylcarbodiimide hydrochloride to yield ethyl 1-(4-carboethoxy-2R-methyl-4R-phenethylbutanoyl) indoline-2S-carboxylate having Rf=0.6 (9:1 $CHCl_3-CH_3OH/SiO_2$).

To a solution of 87 mg of the above diester in 4 ml of methanol at room temperature is added 0.2 ml of 2.2 N aqueous potassium hydroxide, 1.5 ml of water and the reaction mixture is stirred at room temperature for 2 hours. The reaction mixture is worked up in the usual manner (see Example 12) to yield 1-(4-carboethoxy-2R-methyl-4R-phenethylbutanoyl)indoline-2S-carboxylic acid purified as the dicyclohexylamine salt melting at 145°-8° and identical to compound of example 13.

Further basic hydrolysis as follows yields 1-(4-carboxy-2R-methyl-4R-phenethylbutanoyl)indoline-2S-carboxylic acid. To a solution of 0.28 g of 1-(4-carboethoxy-2R-methyl-4R-phenethyl-butanoyl)indoline-2S-carboxylic acid in 3 ml of methanol are added 2 ml of 1N aqueous lithium hydroxide. The reaction mixture is stirred at 55° for 6 hours and then evaporated. The residue in 30 ml of water is washed with 15 ml of diethyl ether. The aqueous layer is acidified to pH 2 with 1N aqueous hydrochloric acid and extracted with 3×25 ml of methylene chloride. These combined organic portions are dried over magnesium sulfate and evaporated. The residue is crystallized from pentane to give 1-(4-carboxy-2R-methyl-4R-phenethylbutanoyl)indoline-2S-carboxylic acid melting at 137°-139°. $[\alpha]_D = -62°$ (c=0.25 in chloroform).

EXAMPLE 15

Preparation of 10,000 tablets each containing 5 mg of the active ingredient of Example 5:

| Formula: | |
|---|---|
| 1-[4-carboxy-4-(2-phenethyl)-butanoyl]-indoline-2S-carboxylic acid | 50.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 16

Preparation of 10,000 capsules each containing 10 mg of the active ingredient of Example 2:

| Formula | |
|---|---|
| 1-(4-carboethoxy-2R,4R-dimethylbutanoyl) indoline-2S-carboxylic acid | 100.0 g |
| Lactose | 1,800.0 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine. Analogously tablets or capsules are prepared from the remaining compounds of the invention, e.g., those illustrated by the other examples herein.

EXAMPLE 17

To a solution of 0.78 g of ethyl indoline-2S-carboxylate hydrochloride, 0.90 g of 4R-carboethoxy-6-phenylhexanoic acid, and 0.48 ml of triethylamine in 40 ml of methylene chloride are added 0.72 g of 1-(3-dimethylaminopropyl)-3-ethylcarbodiimide hydrochloride. The reaction mixture is stirred at room temperature for 4 days. 300 ml of diethyl ether is added and the mixture is washed with 25 ml of water, 25 ml of 2N aqueous hydrochloric acid and 25 ml of saturated aqueous sodium bicarbonate solution. The organic layer is dried over magnesium sulfate and evaporated to give ethyl 1-(4-carboethoxy-4R-phenethylbutanoyl)-indoline-2S-carboxylate with $[\alpha]_D = -64.3°$ (c=0.85 in chloroform).

The starting material for the above procedures is prepared as follows:

8.10 g of N-(4-phenylbutanoyl)-L-prolinol in 50 ml of tetrahydrofuran are added to 71 mMol of lithium diisopropylamide in 270 ml of tetrahydrofuran at −20°. After 1 hour 3.1 ml of allyl bromide are added. After 1 hour at −20° the reaction mixture is diluted with 250 ml of diethyl ether. The layers are separated and the organic phase is washed with 200 ml of 0.5N aqueous hydrochloric acid and 200 ml of saturated aqueous sodium chloride solution, dried over sodium sulfate, and evaporated to give the N-(2R-allyl-4-phenyl-butanoyl)-L-prolinol having $[\alpha]_D = -23.5°$ (c=1 in methanol).

A solution of 7.65 g of N-(2R-allyl-4-phenyl-butanoyl)-L-prolinol in 350 ml of 10% ethanolic sulfuric acid is refluxed for 10 hours. The solvent is evaporated and the residue is partitioned between 100 ml of water and 200 ml of diethyl ether. The layers are separated and the organic phase is washed with 50 ml of saturated aqueous sodium bicarbonate solution, dried over sodium sulfate and evaporated to give the ethyl 2R-allyl-4-phenyl-butyrate having $R_f=0.42$ (9:1 hexane:ether/SiO$_2$).

To 22.2 ml of 1M borane in tetrahydrofuran at 0° C. is added 3.1 g of 2-methyl-2-butene. After 2 hours at 0°, 4.7 g of ethyl 2R-allyl-4phenyl-butyrate are added. After 2 hours 7.3 ml of 3N aqueous sodium hydroxide solution and 7.3 ml of 30% aqueous hydrogen peroxide are added. After 30 minutes the reaction mixture is diluted with 75 ml of diethyl ether. The layers are separated and the aqueous layer is extracted with 2×25 ml of diethyl ether. The combined ether extracts are washed with 25 ml of 1% aqueous sodium carbonate solution and 25 ml of saturated aqueous sodium sulfite solution. The organic phase is dried over magnesium sulfate and evaporated to give ethyl 5-hydroxy-2R-phenethyl-pentanoate with NMR peaks at 7.3, 4.25, 3.61, 1.55–2.78 and 1.27 ppm.

To 4.97 g of ethyl 5-hydroxy-2R-phenethyl-pentanoate in 100 ml of dimethylformamide is added 37.4 g of pyridinium dichromate. The reaction mixture is stirred overnight at room temperature and then poured into 300 ml of ice water. The mixture is extracted with 5×100 ml of diethyl ether. The combined organic portions are washed with 100 ml of 5% aqueous sodium carbonate solution. The aqueous phase is acidified with concentrated sulfuric acid to pH 2 and extracted with 3×100 ml of diethyl ether. These ether extracts are dried over magnesium sulfate and evaporated to give 4R-carboethoxy-6-phenyl-hexanoic acid with $[\alpha]_D=+4.32°$ (c=1 in methanol).

EXAMPLE 18

To 1.10 g of ethyl 1-(4-carboethoxy-4R-phenethyl-butanoyl)indoline-2S-carboxylate in 5 ml of ethanol are added 1.07 ml of 2.21N aqueous potassium hydroxide solution. The reaction mixture is stirred at room temperature for 1 hour and then evaporated. The residue in 20 ml of saturated aqueous sodium bicarbonate solution is washed with 20 ml of diethyl ether. The aqueous layer is adjusted to pH=1 with 2 N aqueous hydrochloric acid and extracted with 2×25 ml of methylene chloride. The combined methylene chloride portions are dried over magnesium sulfate and evaporated to give 1-(4-carboethoxy-4R-phenethylbutanoyl)-indoline-2S-carboxylic acid melting at 100°–102°, $[\alpha]_D=-83.4°$ (c=1.13 in chloroform).

EXAMPLE 19

To 0.67 g of 1-(4-carboethoxy-4R-phenethyl-butanoyl)indoline-2S-carboxylic acid in 8 ml of methanol are added 4.9 ml of 1N aqueous lithium hydroxide solution. The reaction mixture is stirred at 55° for 8 hours and then evaporated. The residue in 30 ml of saturated aqueous sodium bicarbonate solution is washed with 25 ml of diethyl ether. The aqueous layer is acidified with 2N aqueous hydrochloric acid and extracted with 2×25 ml of methylene chloride. The combined methylene chloride portions are dried over magnesium sulfate and evaporated. The residue is crystallized from pentane to give 1-(4-carboxy-4R-phenethylbutanoyl)-indoline-2S-carboxylic acid melting at 132°–135°, $[\alpha]_D=-79.1°$ (c=0.81 in chloroform).

EXAMPLE 20

To a solution of 5.0 g of ethyl indoline-2S-carboxylate hydrochloride and 2.2 g of triethylamine in 40 ml of toluene are added 3.1 g of (2R,4R)-dimethylglutaric anhydride. The reaction mixture is stirred at 80° for 4 hours, then cooled to room temperature and washed with 10 ml of 1N hydrochloric acid and 10 ml of water. The organic layer is dried over sodium sulfate and evaporated. The residue is crystallized from diethyl ether-hexane to give ethyl 1-(4-carboxy-2R,4R-dimethylbutanoyl)-indoline-2S-carboxylate melting at 110°–112°, $[\alpha]_D=-156.5°$ (c=0.2 in ethanol).

EXAMPLE 21

To a solution of 6.5 g of ethyl 1-(4-carboethoxy-2-isopropyl-butanoyl)-indoline-2S-carboxylate in 50 ml of methanol are added 52 ml of 1N aqueous sodium hydroxide solution. The reaction mixture is stirred 2 hours at room temperature and then the methanol is evaporated. The aqueous residue is acidified with 5 ml of concentrated hydrochloric acid and extracted with 3×25 ml of methylene chloride. The combined organic portions are dried over sodium sulfate and evaporated. The residue is crystallized from diethyl ether to give 1-(4-carboxy-2-isopropylbutanoyl)-indoline-2S-carboxylic acid melting at 184°–186°, $[\alpha]_D=-81°$ (c=0.2 in ethanol).

The starting material is prepared as follows: A solution of 14.0 g of 2-isopropylglutaric acid in 80 ml of acetyl chloride is stirred at 50° for 2 hours and then evaporated to give 2-isopropylglutaric anhydride with NMR peaks at 0.98, 1.89, 2.43 and 2.85 ppm.

A solution of 4.0 g of 2-isopropylglutaric anhydride in 20 ml of ethanol is refluxed for 3 hours and then evaporated to give 4-carboethoxy-2-isopropylbutyric acid with NMR peaks at 4.76, 2.31, 1.84, 1.21, and 0.95 ppm.

To a solution of 5.62 g of ethyl indoline-2S-carboxylate hydrochloride, 5.0 g of 4-carboethoxy-2-isopropyl-butyric acid and 2.5 g of triethylamine in 80 ml of methylene chloride are added 5.21 g of 1-(3-dimethylaminopropyl)-3-ethylcarbodiimide hydrochloride. The reaction mixture is stirred overnight at room temperature. The reaction mixture is washed with 40 ml of water, 30 ml of 1N hydrochloric acid and 30 ml of saturated aqueous sodium bicarbonate solution, dried and evaporated, to give ethyl 1-(4-carboethoxy-2-isopropyl-butanoyl)-indoline-2S-carboxylate with NMR peaks at 7.16, 6.78, 5.11, 4.22, 3.31, 2.31, 1.98, 1.22 and 0.95 ppm.

EXAMPLE 22

To a solution uf 4.0 g of indoline-2S-carboxylic acid hydrochloride and 2.0 g of triethylamine in 40 ml of toluene are added 2.84 g of 3,3-dimethylglutaric anhydride. The reaction mixture is stirred at 80° for hours and then evaporated. The residue is partitioned between 25 ml of 1N hydrochloric acid and 25 ml of methylene chloride. The organic layer is separated and washed with 20 ml of water and extracted with 2×20 ml of saturated aqueous sodium bicarbonate solution. The bicarbonate extracts are acidified with 5 ml of concentrated hydrochloric acid and extracted with 2×25 ml of methylene chloride. The organic layer is dried over sodium sulfate and evaporated. The residue is crystallized from ether hexane to give 1-(4-carboxy-3,3-dimethylbutanoyl)-indoline-2S-carboxylic acid melting at 132°–133°, $[\alpha]_D = -151°$ (c=0.2 in ethanol).

EXAMPLE 23

To a solution of 1.0 g of 5-chloroindoline-2-carboxylic acid hydrochloride and 0.43 g of triethylamine in 15 ml of toluene are added 0.55 g of 2R,4R-dimethylglutaric anhydride. The reaction mixture is stirred at 80° for 3.5 hours and then evaporated. The residue is partitioned between 20 ml of 1N hydrochloric acid and 20 ml of methylene chloride. The methylene chloride layer is washed with 10 ml of water and then extracted with 2×10 ml of saturated aqueous sodium bicarbonate solution. The bicarbonate extracts are acidified with 2.5 ml of concentrated hydrochloric acid and extracted with 3×10 ml of methylene chloride. These organic extracts are dried over sodium sulfate and evaporated. The residue is dissolved in 7 ml of diethyl ether and 0.4 g of dicyclohexylamine. The product is filtered and recrystallized from ethyl acetate to give 1-(4-carboxy-2R,4R-dimethylbutanoyl)-5-chloroindoline-2-carboxylic acid bisdicyclohexylammonium salt melting at 185°–187°, $[\alpha]_D = -26.50°$ (c=0.2 in ethanol).

Similarly prepared is 1-(4-carboxy-2R,4R-dimethylbutanoyl)-5-methylindoline-2-carboxylic acid bis-dicyclohexylammonium salt melting at 198°–200°, $[\alpha]_D = +0.9°$ (c=0.2 in ethanol).

Also similarly prepared is 1-(4-carboxy-2R,4R-dimethylbutanoyl)-5-methoxyindoline-2S-carboxylic acid melting at 150°–152°, $[\alpha]_D = -130°$ (c=0.2 in ethanol).

The starting materials are prepared as follows:

The mixture of 20 g of 5-methoxyindole-2-carboxylic acid (J. Chem. Soc., 1970, 865) and 200 ml of acetic anhydride is refluxed for 2 hours and allowed to cool to room temperature. It is filtered, the filtrate evaporated and the residue is stirred in 300 ml of water. Excess sodium bicarbonate is added, the mixture stirred for 3 hours and then washed with 200 ml of diethyl ether. The aqueous layer is acidified to pH=1 with concentrated hydrochloric acid and filtration yields the 1-acetyl-5-methoxyindole-2-carboxylic acid melting at 173°–175°.

The solution of 16.5 g thereof in 250 ml of ethanol is hydrogenated at one atmosphere in the presence of 1.0 g of platinum oxide. After 2 hours the mixture is filtered and the filtrate concentrated to 100 ml. After standing at 0° overnight it is filtered, to give the colorless crystalline 1-acetyl-5-methoxyindoline-2-carboxylic acid melting at 164°–167°.

6.0 g thereof are refluxed in 60 ml of 2N aqueous hydrochloric acid for 2 hours and the mixture is evaporated. The residue is dissolved in 50 ml of isopropanol and diethyl ether is added until the solution becomes turbid. After cooling at 0° the precipitate is filtered off, to yield the 5-methoxyindoline-2-carboxylic acid hydrochloride melting at 90°–92° (decomposition).

Other substituted indoline-2-carboxylic acids are similarly prepared i.e., 5-chloroindoline-2-carboxylic acid hydrochloride melting at 165°–167° and 5-methylindoline-2-carboxylic acid hydrochloride melting at 171°–173°.

EXAMPLE 24

To a solution of 1.5 g of 4-cyanobutyric acid, 3.0 g of ethyl indoline-2S-carboxylate hydrochloride and 1.35 g of triethylamine in 75 ml of methylene chloride are added 3.8 g of 1-(3-dimethylaminopropyl)-3-ethylcarbodiimide hydrochloride. The reaction mixture is stirred at room temperature for 3 days. The reaction mixture is washed with 50 ml of water, 50 ml of 2N hydrochloric acid and 50 ml of saturated aqueous sodium bicarbonate solution. The organic layer is dried over magnesium sulfate and evaporated to give the ethyl 1-(4-cyanobutanoyl)-indoline-2S-carboxylate, showing major IR-bands at 2240, 1730 and 1660 cm$^{-1}$.

To 2.3 g of ethyl 1-(4-cyanobutanoyl)-indoline-2S-carboxylate in 30 ml of tetrahydrofuran and 10 ml of water are added 8.8 ml of 1N aqueous lithium hydroxide solution. The reaction mixture is stirred overnight at room temperature. The reaction mixture is diluted with 50 ml of water and washed with 50 ml of diethyl ether. The aqueous layer is acidified with 10 ml of 2N hydrochloric acid and extracted with 2×50 ml of diethyl ether. These extracts are dried over magnesium sulfate and evaporated to give 1-(4-cyanobutanoyl)-indoline2S-carboxylic acid melting at 98°–100°, $[\alpha]_D = -112.6°$ (c=0.9 in ethanol).

A solution of 2.6 g of 1-(4-cyanobutanoyl)-indoline-2S-carboxylic acid in 50 ml of ethanol and 50 ml of ether at 0° is saturated with hydrogen chloride gas. The reaction mixture is then stirred at room temperature for 1 hour. The reaction mixture is cooled to 0° and 50 ml of water is added. After 10 minutes the reaction mixture is concentrated under reduced pressure and the residue is taken up in 50 ml of water and extracted with 2×50 ml of ether. The combined ether portions are dried over magnesium sulfate and evaporated. Crystallization of the residue from ether-hexane gives ethyl 1-(4-carboethoxybutanoyl)-indoline-2S-carboxylate melting at 72°–73°, $[\alpha]_D = -81.7°$ (c=0.35 in ethanol).

EXAMPLE 25

Indoline-2S-carboxylic acid hydrochloride (201.44 g) and pyridine (790 ml) are charged into a 2 lt. three-neck, round bottom flask equipped with mechanical stirring, addition funnel (nitrogen inlet), condenser (with Drierite tube for nitrogen outlet), and nitrogen atmosphere. This stirred solution is cooled with an ice bath while 4-(carboethoxy)-2R,4R- dimethylbutanoyl chloride (189.6 g) is added slowly over twenty minutes. After ten minutes more, the ice bath is removed and the reaction is stirred vigorously with a stream of nitrogen flowing over it for an additional three hours. Most of the pyridine is removed at room temperature with a rotary evaporator connected to a vacuum pump (0.1 mm Hg) and then the residue is cooled in an ice bath and acidified slowly with 200 ml of concentrated hydrochloric acid to pH ca. 2. This solution is extracted with 3×200 ml of methylene chloride and the organic extracts are washed with 200 ml of 3N hydrochloric acid, 200 ml of water, and treated with magnesium sulfate and Florisil. Filtration and evaporation on a rotary evaporator and then high vacuum pump (temperature up to 40°) affords crude product, which crystallizes further on standing, m.p. 114°–117°, $[\alpha]_D^{25} = -159.6$ (c=0.663, ethanol). This product is stirred for two hours in anhydrous ether. The product is then filtered and washed with ether, and dried for sixty hours under vacuum to give the purified compound of Example 8a), 1-(4-carboethoxy-2R,4R-dimethylbutanoyl)-indoline-2S-carboxylic acid, m.p. 128°–30°, $[\alpha]_D^{25} = -162.8°$ (c=0.908, ethanol).

The starting material is prepared as follows:

2R,4R-Dimethylglutaric anhydride, [m.p. 42°–4°, $[\alpha]_D^{25} = +56.45°$ (c=1.038 in chloroform)] (178.65 g) and absolute ethanol (357.3 ml) are charged into a 1000 ml round bottom, one-neck flask equipped with a condenser, nitrogen atmosphere, and magnetic stirrer. Nitrogen is bubbled through the stirred solution for one hour. The mixture is then brought to reflux and stirred at this temperature under nitrogen overnight. After cooling, the excess ethanol is removed on the rotary evaporator (bath temperature up to 45°) and is dried further at 0.1 mm Hg for four hours with occasional warming and stirring to afford an oil which is dissolved in ether (200 ml) and extracted with a saturated sodium bicarbonate solution (5×200 ml). The basic aqueous solution is cooled with an ice bath, then acidified slowly with concentrated hydrochloric acid (110 ml) to a pH ca. 2, and then saturated with solid sodium chloride. This mixture is extracted with ethyl acetate (5×200 ml). The ethyl acetate extracts are dried over sodium sulfate, filtered and the solvent is removed on the rotary evaporator and then at 0.1 mm Hg at room temperature for two hours with stirring to obtain 4-carboethoxy-2R,4R-dimethylbutanoic acid, $[\alpha]_D^{25} = -44.1°$ (c=1.435, ethanol).

The above 4-(carboethoxy)-2R,4R-dimethylbutyric acid (174.75 g) is charged into a 1000 ml round bottom flask equipped with magnetic stirring, addition funnel, and a nitrogen atmosphere. The stirred reaction is cooled with an ice bath and oxalyl chloride (245 ml) is added slowly over 20 minutes. The mixture is stirred an additional 40 minutes with ice bath cooling and is then stirred two hours at room temperature under a nitrogen atmosphere. The excess oxalyl chloride is evaporated on a rotary evaporator and the residue is then placed under high vacuum (0.1 mm Hg, room temperature) for one hour to yield the 4-carboethoxy-2R,4R-dimethylbutanoyl chloride, $[\alpha]_D^{25} = -30.1°$ (c=0.916, chloroform), which is used directly in the above condensation.

EXAMPLE 26

To 1.7 g of 4-(pivaloyloxymethoxycarbonyl)-2R,4R-dimethylbutanoyl chloride in 25 ml of pyridine at room temperature is added indoline-2S-carboxylic acid hydrochloride (1.2 g). The reaction is stirred 3 hours at room temperature and then evaporated. The residue is dissolved in 75 ml of saturated aqueous sodium bicarbonate and washed with 2×50 ml of ether. The aqueous layer is acidified with 10 ml of 2N aqueous hydrochloric acid and extracted with 3×75 ml of methylene chloride. The combined methylene chloride layer is dried over magnesium sulfate and evaporated to give 1-[4-(pivaloyloxymethoxycarbonyl)-2R,4R-dimethylbutanoyl]-indoline-2S-carboxylic acid, m.p. 109°–112° C., $[\alpha]_D = -136.2°$ (c=0.94 in ethanol), NMR (CDCl$_3$): 1.2, 1.8, 2.5, 3.35, 5.1, 5.75, 7.2, 8.3, 9.4 ppm, IR (CHCl$_3$): 3500–3200, 2950, 1740 cm$^{-1}$.

The starting material is prepared as follows:

A mixture of 5.0 g of 2R,4R-dimethylglutaric anhydride and 3.65 ml of benzyl alcohol is stirred at 85° for 3 hours to give 4-(carbobenzyloxy)-2R,4R-dimethylbutanoic acid. NMR (CDCl$_3$): 1.2, 1.8, 2.6, 5.2, 7.4, 11.2 ppm.

The above acid (3.3 g) is treated with 5.9 ml of 2.21 N potassium hydroxide. The solution is evaporated. Toluene (100 ml) is added and the mixture is evaporated to give the potassium 4-(carbobenzyloxy)-2R,4R-dimethylbutanoate.

To chloromethyl pivalate (2.56 g) in 50 ml of acetone is added sodium iodide (2.54 g). The reaction is stirred at room temperature for 3 hours. The reaction is filtered and the filtrate is evaporated. To the residue in 25 ml of dimethylformamide is added potassium 4-(carbobenzyloxy)-2R,4R-dimethylbutanoate (3.7 g) in 25 ml of dimethylformamide. The reaction is stirred at room temperature for 18 hours and then evaporated. The residue is dissolved in 150 ml of ether and washed with 3×50 ml of 10% aqueous sodium bicarbonate and 3×50 ml of saturated aqueous sodium chloride. The organic layer is dried over magnesium sulfate and evaporated to give pivaloyloxymethyl 4-(carbobenzyloxy)-2R,4R-dimethylbutanoate as an oil, NMR (CDCl$_3$):1.2, 1.8, 2.5, 5.2, 5.8, 7.45 ppm.

A solution of 5.3 g of pivaloyloxymethyl 4-(carbobenzyloxy)-2R,4R-dimethylbutanoate in 150 ml of ethanol is hydrogenated at atmospheric pressure in the presence of 0.5 g of 10% palladium on carbon. The reaction is filtered and evaporated to give 4-(pivaloyloxymethoxycarbonyl)-2R,4R-dimethylbutanoic acid, NMR (CDCl$_3$):1.2, 1.7, 2.55, 5.8, 10.3 ppm.

To 1.7 g of the above 4-(pivaloyloxymethoxycarbonyl)-2R,4R-dimethylbutanoic acid in 30 ml of methylene chloride at room temperature is added 1.7 ml of oxalyl chloride. The reaction is stirred at room temperature for 2.5 hours and then evaporated to give 4-(pivaloyloxymethoxycarbonyl)-2R,4R-dimethylbutanoyl chloride, used directly in the above condensation, NMR (CDCl$_3$):1.2, 1.9, 2.8, 5.85 ppm.

EXAMPLE 27

To 6.5 g of 4-(l-bornyloxycarbonylmethoxycarbonyl)-2R,4R-dimethylbutanoic acid in 100 ml of methylene chloride is added 9.0 ml of oxalyl chloride. After stirring 3 hours at room temperature the reaction is evaporated. The residue is dissolved in 70 ml of pyridine and indoline-2S-carboxylic acid hydrochloride (3.7 g) is added. The reaction is stirred 2.5 hours at room temperature. The residue is evaporated. The residue is dissolved in 75 ml of saturated aqueous sodium bicarbonate and washed with 3×50 ml of ether. The aqueous layer is acidified with 10 ml of 6N hydrochloric acid and extracted with 3×75 ml of methylene chloride. The combined methylene chloride portions are dried over magnesium sulfate and evaporated to give 1-4-(l-bornyloxycarbonylmethoxycarbonyl)-2R,4R-dimethylbutanoyl-indoline-2S-carboxylic acid, m.p. 65°–67° with $[\alpha]_D = -139°$ (c=0.915 in ethanol), NMR (CDCl$_3$):3.4, 4.9, 7.1–8.4 ppm, IR (CHCl$_3$):3500–3100, 2950, 1735 cm$^{-1}$.

The starting material is prepared as follows:

A mixture of 5.0 g of l-borneol and 7.74 ml of chloroacetyl chloride is stirred at 100° for 3 hours and then evaporated to give l-bornyl chloroacetate as an oil, NMR (CDCl$_3$):0.88, 0.91, 1.1–2.5, 4.1, 5.0 ppm.

To 5.0 g of the above l-bornyl chloroacetate in 70 ml of acetone is added sodium iodide (3.4 g). The reaction is stirred 3 hours at room temperature and then filtered and evaporated to give l-bornyl iodoacetate, which is used directly in the next step.

l-Bornyl iodoacetate (6.7 g) and potassium 4-(carbobenzyloxy)-2R,4R-dimethylbutanoate (6.1 g) are combined in 100 ml of dimethylformamide. The reaction is stirred at room temperature overnight and then evaporated. The residue is dissolved in 200 ml of ether and washed with 2×50 ml of saturated aqueous sodium bicarbonate and 50 ml of brine. The organic layer is dried over magnesium sulfate and evaporated to give l-bornyloxycarbonylmethyl-4-(carbobenzyloxy)-

2R,4R-dimethylbutanoate, NMR (CDCl$_3$):4.6, 5.1, 7.4 ppm.

l-Bornyloxycarbonylmethyl 4-(carbobenzyloxy)-2R,4R-dimethylbutanoate (8.0 g) in 125 ml of ethanol is hydrogenated at one atmosphere in the presence of 0.8 g of 10% palladium on carbon. The reaction is filtered and evaporated to give 4-(l-bornyloxycarbonylmethoxycarbonyl)-2R,4R-dimethylbutanoic acid; NMR (CDCl$_3$):4.6, 5.0, 8.2 ppm.

EXAMPLE 28

4-[(L-2-Acetoxymethylpyrrolidino)-carbonyl]-2R,4R-dimethylbutanoic acid, (3.6 g) in 7 ml of oxalyl chloride is stirred at room temperature for 3 hours and then evaporated. The acid chloride is dissolved in 50 ml of pyridine and indoline-2S-carboxylic acid hydrochloride (2.76 g) is added. The reaction is stirred for 2 hours at room temperature and then is evaporated. The residue is dissolved in 50 ml of saturated aqueous sodium bicarbonate and washed with 3×50 ml of ether. The aqueous layer is acidified with 10 ml of 6N aqueous hydrochloric acid and extracted with 3×50 ml of methylene chloride. The combined methylene chloride portions are dried over magnesium sulfate and evaporated to give 1-(4-[L-2-acetoxymethylpyrrolidino)carbonyl]-2R,4R-dimethylbutanoyl)-indoline-2S-carboxylic acid, m.p. 109°–112°, $[\alpha]_D = -172.4°$ (c=1.03 in ethanol), NMR (CDCl$_3$):1.2, 4.9, 7.1, 8.3, 9.2 ppm, IR (CHCl$_3$):3500–3100, 2950, 1730 cm$^{-1}$.

The starting material is prepared as follows:

To 4-(Carbobenzyloxy)-2R,4R-dimethylbutanoic acid (3.9 ml) in 50 ml of methylene chloride is added 4.1 ml of oxalyl chloride. The reaction is stirred at room temperature for 3 hours and then evaporated to give 4-(carbobenzyloxy)-2R,4R-dimethylbutanoyl chloride which is used directly in the next step.

To a mixture of L-prolinol (1.42 g) in 35 ml of methylene chloride and 17.7 ml of 1N aqueous sodium hydroxide at 0° is added the above acid chloride (4.3 g). The reaction is stirred for 4 hours at 0° and then 1 hour at room temperature. The layers are separated and the aqueous layer is washed with 2×35 ml of methylene chloride. The combined organic portions are washed with 2×40 ml of 2N aqueous hydrochloric acid, dried with magnesium sulfate and evaporated to give benzyl 4-[L-2-hydroxymethylpyrrolidino)-carbonyl]-2R,4R-dimethylbutanoate, NMR (CDCl$_3$):1.05, 1.2, 5.1, 7.35 ppm.

The above amide (4.5 g) is stirred in 3 ml of acetyl chloride at reflux for 3 hours. The reaction is then evaporated to give benzyl 4-[L-2-acetoxymethylpyrrolidino)-carbonyl]-2R,4R-dimethylbutanoate, NMR (CDCl$_3$):1.07, 1.15, 2.0, 5.17, 7.4 ppm.

Benzyl 4-[(L-2-acetoxymethylpyrrolidino)-carbonyl]-2R,4R-dimethylbutanoate (4.6 g) in 100 ml of ethanol is hydrogenated at one atmosphere in the presence of 0.5 g of 10% palladium on carbon. The reaction is filtered and the filtrate is evaporated to give 4-[L-2-acetoxymethylpyrrolidino)carbonyl]-2R,4R-dimethylbutanoic acid, NMR (CDCl$_3$):1.2, 2.03 ppm.

EXAMPLE 29

1-(4-[(L-2-acetoxymethylpyrrolidino)-carbonyl]-2R,4R-dimethylbutanoyl)-indoline-2S-carboxylic acid (1.5 g) in 100 ml of methanol is added 1.2 g of potassium carbonate. The reaction is stirred overnight at room temperature. The reaction is evaporated and the residue in 150 ml of methylene chloride is acidified with 75 ml of 2N aqueous hydrochloric acid. The layers are separated and the organic layer is washed with 75 ml of brine, dried over magnesium sulfate and then evaporated to give 1-(4-[N-(L-2-hydroxymethylpyrrolidino)-carbonyl]-2R,4R-dimethylbutanoyl)-indoline-2S-carboxylic acid, m.p. 95°–99°, $[\alpha]_D = -179.3°$ (c=0.98 in ethanol), NMR (CDCl$_3$):1.1, 4.2, 4.9 ppm, IR (CHCl$_3$):3500–3100, 2950, 1730 cm$^{-1}$.

EXAMPLE 30

To 1,1'-carbonyldiimidazole (1.14 g) in 20 ml of methylene chloride at 0° is added 4-($\beta$-methoxyethoxymethoxycarbonyl)-2R,4R-dimethylbutanoic acid (1.6 g) in 20 ml of methylene chloride. After 1 hour indoline-2S-carboxylic acid hydrochloride (1.3 g) in 10 ml of pyridine is added dropwise over 10 minutes. The reaction is stirred at room temperature overnight. The reaction is evaporated. The residue is dissolved in 75 ml of methylene chloride and washed with 2×25 ml of 2N aqueous hydrochloric acid. The organic layer is dried over magnesium sulfate and evaporated to give crude product. The product is dissolved in 20 ml of ether, 20 ml of ethyl acetate and 0.46 ml of dicyclohexylamine are added, followed by 25 ml of pentane. The product was collected by filtration to give 1-[4-($\beta$-methoxyethoxymethoxycarbonyl )-2R,4R-dimethylbutanoyl]-indoline-2S-carboxylic acid as the dicyclohexylammonium salt, mp 159°–161°, $[\alpha]_D = -78.6°$ (c=1.13, EtOH).

The starting material is prepared as follows:

To 4 g of 4-(carbobenzyloxy)-2R,4R-dimethylbutanoic acid in 60 ml of ether at 0° is added 1.8 g of potassium t-butoxide. After 30 minutes $\beta$-methoxyethoxymethyl chloride (1.82 g) is added. The reaction is allowed to warm to room temperature over 1 hour and then stirred an additional 2 hours at room temperature. The reaction is poured into 50 ml of saturated aqueous sodium bicarbonate and extracted with 3×50 ml of ether. The combined ether portions are dried (magnesium sulfate) and evaporated to give $\beta$-methoxyethoxymethyl 4-(carbobenzyloxy)-2R,4R-dimethylbutanoate as an oil, $[\alpha]_D = -32.6°$ (c=1.19 in ethanol), NMR:80, 3.35, 5.16, 5.30 ppm.

A solution of the above ester (0.5 g) in 25 ml of ethanol is hydrogenated at 1 atmosphere pressure and room temperature in the presence of 50 mg of 10% palladium on carbon. After 2 hours the reaction is filtered. The filtrate is evaporated to give $\beta$-methoxyethoxymethyl 2R,4R-dimethylbutanoic acid as an oil, $[\alpha]_D = -25.7°$ (c=0.975 in ethanol); NMR:1.20, 1.83, 3.40, 5.40 ppm.

EXAMPLE 31

To 4-(3-phthalidoxycarbonyl)-2R,4R-dimethylbutanoyl chloride (2.5 g) in 45 ml of pyridine is added indoline-2S-carboxylic acid hydrochloride (1.3 g). The reaction is stirred at room temperature for 3 hours. The reaction is evaporated and the residue in 100 ml of methylene chloride is washed with 2×50 ml of water. The combined aqueous portions are adjusted to pH 1 with concentrated aqueous hydrochloric acid and extracted with 3×25 ml of methylene chloride. The combined methylene chloride portions are washed with 3×25 ml of methylene chloride. The combined methylene chloride portions are washed with 2×25 ml of 2N aqueous hydrochloric acid, dried over magnesium sulfate and evaporated to give a foam, which is crystallized to give 1-[4-(3-phthalidoxycarbonyl)-2R,4R-dimethylbutanoyl]-indoline-2S-carboxylic acid, m.p. 119°–122°; $[\alpha]_D = -104.9°$ (c=0.65, EtOH).

The starting material is prepared as follows:

A solution of 4-(carbobenzyloxy)-2R,4R-dimethylbutanoic acid (0.3 g) in 6 ml of 2N aqueous potassium hydroxide is evaporated to dryness. The residue is twice evaporated with 20 ml of toluene. To the residue in 50 ml of dimethylformamide is added 3-bromophthalide (2.55 g). The reaction is stirred overnight at room temperature. The reaction is evaporated. The residue in 40 ml of ether is washed with 2×20 ml of saturated aqueous sodium bicarbonate. The ether layer is dried over magnesium sulfate and evaporated to give benzyl 4-(3-phthalidoxycarbonyl)-2R,4R-dimethylbutanoate as an oil, NMR (CDCl$_3$) 1.85, 2.60, 3.50, 5.15 ppm; IR (film) 3035, 2978, 1775, 1755, 1730, 1468 cm$^{-1}$.

The above ester (3.5 g) in 45 ml of ethanol is hydrogenated at 1 atmosphere pressure and room temperature in the presence of 350 mg of 10% palladium on carbon. After 3 hours the reaction is filtered. The filtrate is evaporated to give 4-(3-phthalidoxycarbonyl)-2R,4R-dimethylbutanoic acid $[\alpha]_D = -21.3°$ (c=0.78 in ethanol); NMR 1.2, 1.8, 2.65, 3.70 ppm.

To 4-(3-phthalidoxycarbonyl)-2R,4R-dimethylbutanoic acid (0.30 g) in 10 ml of methylene chloride is added 0.24 ml of oxalyl chloride. The reaction is stirred at room temperature for 3 hours and then evaporated to give 4-(3-phthlidoxycarbonyl)-2R,4R-dimethylbutanoyl chloride, $[\alpha]_D = -16.1°$ (c=0.53 in chloroform); NMR 1.3, 1.9, 2.76, 4.3 ppm.

EXAMPLE 32

To indoline-2S-carboxylic acid hydrochloride (2.23 g) in 30 ml of pyridine at room temperature is added 4-(carbobenzyloxy)-2R,4R-dimethylbutanoyl chloride (3.3 g). After stirring for 3 hours at room temperature the reaction is evaporated. The residue is dissolved in 100 ml of saturated aqueous sodium bicarbonate and washed with 50 ml of ether. The aqueous layer is adjusted to pH 1 with concentrated hydrochloric acid and extracted with 3×50 ml of methylene chloride. The combined methylene chloride portions are stirred over florisil, dried over magnesium sulfate and evaporated to give 1-[4-(carbobenzyloxy)-2R,4R-dimethylbutanoyl]-indoline-2S-carboxylic acid, m.p. 150°-153°, $[\alpha]_D = -139.1°$ (c=0.79 in ethanol).

The starting material is prepared as follows:

The above acid chloride is prepared by stirring 3.0 g of 4-(carbobenzyloxy)-2R,4R-dimethylbutanoic acid and oxalyl chloride (1.05 ml) in 50 ml of methylene chloride for 3 hours at room temperature and then evaporating the solvent to give the 4-carbobenzyloxy-2R,4R-dimethylbutanoyl chloride, used directly in the preceding condensation.

EXAMPLE 33

To L-phenylalanine methyl ester hydrochloride (1.3 g) and 1-(4-carboethoxy-2R,4R-dimethylbutanoyl)-indoline-2S-carboxylic acid (2.0 g) in 50 ml of methylene chloride at room temperature is added 0.84 ml of triethylamine and 1.3 g of 1-(3-dimethylaminopropyl)-3-ethylcarbodiimide hydrochloride. The reaction is stirred at room temperature for 20 hours. The reaction is washed with 3×25 ml of 2N aqueous hydrochloric acid, 2×25 ml of saturated aqueous sodium bicarbonate and 25 ml of brine. The organic layer is dried over magnesium sulfate and evaporated to give N-[1-(4-carboethoxy-2R,4R-dimethylbutanoyl)-indolinyl-2S-carbonyl]-L-phenylalanine methyl ester, mp 110°-113°, $[\alpha]_D = -119.7°$ (c=0.75 in ethanol).

EXAMPLE 34

To 2.4 g of N-[1-(4-carboethoxy-2R,4R-dimethylbutanoyl)-indolinyl-2S-carbonyl]-L-phenylalanine methyl ester in 35 ml of ethanol is added 9 ml of 1N sodium hydroxide and 10 ml of water. The reaction is stirred overnight at room temperature. The ethanol is evaporated and the aqueous solution is washed with 10 ml of ether and then acidified to pH 1 with 2N aqueous hydrochloric acid. The solution is extracted with 3×30 ml of ethyl acetate. The combined ethyl acetate portions are dried over magnesium sulfate and evaporated to give N-[1-(4-carboxy-2R,4R-dimethylbutanoyl)-indolinyl-2S-carbonyl]-L-phenylalanine, mp 161°-164°; $[\alpha]_D = -104.3°$ (c=1.15 in ethanol).

EXAMPLE 35

A mixture of the acid chloride obtained from 1.8 g of 4-(α-carboethoxy-ethoxycarbonyl)-2R,4R-dimethylbutanoic acid, and indoline-2S-carboxylic acid hydrochloride (1.3 g) in 25 ml of pyridine is stirred at room temperature for 3 hours and then evaporated. The residue in 50 ml of saturated aqueous sodium bicarbonate is washed with 2×30 ml of ether. The aqueous layer is acidified to pH 1 with solid potassium bisulfate and extracted with 2×30 ml of methylene chloride. The combined methylene chloride portions are stirred over florisil and dried with magnesium sulfate and evaporated to give an oil. Trituration with 10 ml of ether gives 1-[4-(α-carboethoxy-ethoxycarbonyl)-2R,4R-dimethylbutanoyl]-indoline-2S-carboxylic acid, mp 151°-154°, $[\alpha]_D = -146.8°$ (c−1.06 in ethanol).

The starting material is prepared as follows:

A mixture of 2R,4R-dimethylglutaric anhydride (1.0 g) and ethyl l-lactate (0.809 ml) is heated at 80° for 4 days. The crude 4-(α-carboethoxy-ethoxycarbonyl)-2R,4R-dimethylbutanoic acid is used directly, R$_f$-0.7 (silica gel-ethyl acetate), NMR (CDCl$_3$) 5.05, 4.28, 2.58, 1.79, 1.16 ppm.

The above acid (1.8 g) in 30 ml of methylene chloride is stirred with 2 ml of oxalyl chloride for 3 hours at room temperature. Evaporation of the solvent gives 4-(α-carboethoxyethoxycarbonyl)-2R,4R-dimethylbutanoyl chloride as used above.

EXAMPLE 36

To the acid chloride, obtained from 2.5 g of 2R,4R-dimethylglutaric anhydride as described below, in 40 ml of pyridine is added indoline-2S-carboxylic acid hydrochloride (3.2 g). The reaction is stirred 3 hours at room temperature and then evaporated. The residue in 50 ml of water is washed with 3×50 ml of methylene chloride. The aqueous layer is adjusted to pH 3.0 with 2N aqueous hydrochloric acid and extracted with 3×50 ml of ethyl acetate. The combined ethyl acetate portions are dried over magnesium sulfate and evaporated. The residue is triturated with 50 ml of ether to give the crude 1-[4-(3-pyridylmethoxycarbonyl)-2R,4R-dimethylbutanoyl]-indoline-2S-carboxylic acid which is dissolved in 30 ml of 3N aqueous hydrochloric acid and washed with 30 ml of ethyl acetate. The aqueous layer is evaporated and the residue dried in vacuo at 50° to give 1-[4-(3-pyridylmethoxycarbonyl)-2R,4R-dimethylbutanoyl]indoline-2S-carboxylic acid hydrochloride, mp 86°-89°, $[\alpha]_D = -75.2°$ (c=0.8 in ethanol).

The starting material is prepared as follows:

A mixture of 2R,4R-dimethylglutaric anhydride (2.5 g) and 3-pyridylcarbinol (1.7 ml) are stirred at 90° for 6 hours. The reaction is cooled to give the crude 4-(3-pyridylmethoxycarbonyl-2R,4R-dimethylbutanoic acid, NMR (CDCl$_3$), 8.83, 7.86, 7.44, 5.19, 2.58, 1.75, 1.18 ppm, IR (film) 2980, 2935, 1735, 1465, 1163 cm$^{-1}$.

The above acid in 50 ml of methylene chloride is stirred with 4.5 ml of oxalyl chloride for 3 hours at room temperature. Evaporation of the solvent gives the acid chloride, used without further purification.

EXAMPLE 37

To ethyl 1-(4-carboxy-2R,4R-dimethylbutanoyl)-indoline-2S-carboxylate (2.5 g) and β-carbobenzyloxyaminoethylamine (1.6 g) in 50 ml of methylene chloride is added 1.05 ml of triethylamine and 1.6 g of 1-(3-dimethylaminopropyl)-3-ethylcarbodiimide. The reaction is stirred for 2 days at room temperature and then refluxed 4 hours. The reaction is washed with 2×25 ml of 2N aqueous hydrochloric acid and 2×25 ml of saturated aqueous sodium bicarbonate. The methylene chloride layer is dried over magnesium sulfate and evaporated to give ethyl 1-[4-(β-carbobenzyloxyamino-N-ethylcarbamoyl)-2R,4R-dimethylbutanoyl]-indoline-2S-carboxylate after trituration with ethyl ether; R$_F$=0.4 (silica gel-ethyl acetate), NMR (CDCl$_3$) 7.41, 5.11, 4.13, 1.15 ppm.

EXAMPLE 38

To ethyl 1-[4-(β-carbobenzyloxyamino-N-ethylcarbamoyl)-2R,4R-dimethylbutanoyl]-indoline-2S-carboxylate (2.4 g) in 25 ml of ethanol is added 5.2 ml of 1N sodium hydroxide in 10 ml of water. The reaction is stirred 4 hours at room temperature. The reaction is evaporated to remove ethanol. The aqueous residue is diluted to 100 ml with water and washed with 2×10 ml of ether, acidified to pH 1 with solid potassium bisulfate and extracted with 3×25 ml of methylene chloride. The combined methylene chloride extracts are dried with magnesium sulfate and evaporated. The residue is slurried in 40 ml of ether to give 1-[4-(β-carbobenzyloxyamino-N-ethylcarbamoyl)-2R,4R-dimethylbutanoyl]-indoline-2S-carboxylic acid, m.p. 104°–106°, NMR (CDCl$_3$) 8.39, 7.36, 7.2, 6.15, 5.02 ppm.

EXAMPLE 39

A solution of 0.82 g of 1-[4-(β-carbobenzyloxyamino-N-ethylcarbamoyl)-2R,4R-dimethylbutanoyl]-indoline-2S-carboxylic acid in 35 ml of ethanol is hydrogenated at 1 atmosphere pressure in the presence of 70 mg of 10% palladium on carbon for 3 hours at room temperature. The reaction is filtered and the filtrate is evaporated to give 1-[4-(β-amino-N-ethylcarbamoyl)-2R,4R-dimethylbutanoyl]-indoline-2S-carboxylic acid, mp 202°–204°, $[\alpha]_D$=−99.5° (c=0.86 in ethanol).

EXAMPLE 40

To 1.9 g of the potassium salt of 1-[4-(carbobenzyloxy)-2R,4R-dimethylbutanoyl]-indoline-2S-carboxylic acid in 35 ml of dimethylformamide at room temperature is added 1.15 g of iodomethyl pivalate. The reaction is stirred overnight at room temperature. The reaction is evaporated and the residue is taken up in 150 ml of ether and washed with 50 ml of saturated aqueous sodium bicarbonate and 50 ml of brine. The organic layer is dried (magnesium sulfate) and evaporated to give pivaloyloxymethyl 1-[4-(carbobenzyloxy)-2R,4R-dimethylbutanoyl]-indoline-2S-carboxylate, NMR (CDCl$_3$) 1.20, 3.20, 5.70, 7.25 ppm; R$_f$=0.8 (90:9:1, CHCl$_3$:EtOH:HOAc, silica gel).

EXAMPLE 41

A solution of 0.60 g of pivaloyloxymethyl 1-[4-(carbobenzyloxy)-2R,4R-dimethylbutanoyl]-indoline-2S-carboxylate in 30 ml of ethanol is hydrogenated at room temperature and one atmosphere pressure in presence of 50 mg of 10% palladium on carbon. The reaction is filtered and the filtrate is evaporated to give pivaloyloxymethyl 1-[4-carboxy-2R,4R-dimethylbutanoyl]-indoline-2S-carboxylate, mp 143°–145°, $[\alpha]_D$=−139.6° (c=0.9 in ethanol).

EXAMPLE 42

To 2.4 g of ethyl 1-(4-carboxy-2R,4R-dimethylbutanoyl)indoline-2S-carboxylate in 100 ml of methylene chloride is added 1.0 g of glycine ethyl ester hydrochloride, 1.0 ml of triethylamine and 1.5 g of 1-(3-dimethylaminopropyl)-3-ethylcarbodiimide hydrochloride. The reaction is stirred overnight at room temperature. The reaction is washed with 50 ml of 2N aqueous hydrochloric acid and 50 ml of saturated aqueous sodium bicarbonate. The organic layer is dried over magnesium sulfate and evaporated to give ethyl 1-[4-(carboethoxymethylcarbamoyl)-2R,4R-dimethylbutanoyl]-indoline-2S-carboxylate, $[\alpha]_D$=−83.6° (c=0.78 in ethanol), NMR (CDCl$_3$) 1.30, 4.20, 5.20, 7.25 ppm.

EXAMPLE 43

To 2.3 g of ethyl 1-[4-(carboethoxymethylcarbamoyl)-2R,4R-dimethylbutanoyl]-indoline-2S-carboxylate in 40 ml of ethanol at room temperature is added 6.0 ml of 2N aqueous potassium hydroxide followed by 15 ml of water. The reaction is stirred at room temperature for 3 hours. The ethanol is removed by evaporation and the aqueous portion is washed with 2×10 ml of ether. The aqueous layer is adjusted to pH 1 by addition of solid potassium bisulfate and extracted with 3×25 ml of methylene chloride. The combined methylene chloride portions are dried over magnesium sulfate and evaporated to give 1-[4-carboxymethylcarbamoyl)-2R,4R-dimethylbutanoyl]-indoline-2S-carboxylic acid, m.p. 70°–73°, $[\alpha]_D$=86.5° (c=0.75 in ethanol).

EXAMPLE 44

A solution of 1-(4-carboxy-2R,4R-dimethylbutanoyl)indoline-2S-carboxylic acid (250 mg) in 20 ml of ethanol is hydrogenated at 3 atmospheres pressure in the presence of 100 mg of 5% rhodium on carbon at room temperature for 18 hours. The reaction is filtered and the filtrate is evaporated to give 1-(4-carboxy-2R,4R-dimethylbutanoyl)-octahydroindole-2S-carboxylic acid, mp 83°–86°, $[\alpha]_D$=−95.5° (c=0.67 in ethanol).

EXAMPLE 45

A solution of 1-(4-carboethoxy-2R,4R-dimethylbutanoyl)-indoline-2S-carboxylic acid (1.5 g) in 100 ml of ethanol is hydrogenated at 3 atmospheres pressure in the presence of 500 mg of 5% rhodium on carbon at room temperature for 3 days. The reaction is filtered and the filtrate is evaporated to give 1-(4-carboethoxy-2R,4R-dimethylbutanoyl)-octahydroindole-2S-carboxylic acid, mp 50°–53°, $[\alpha]_D$=−95.0° (c=1.04 in ethanol).

I claim:

1. A mono- or bis-functional derivative of an indoline-2-carboxylic acid of the formula I

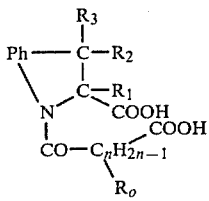

(I)

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_o$ is hydrogen or HPh; each of $R_1$, $R_2$ and $R_3$ is hydrogen or lower alkyl; and n is an integer from 2 to 8;

said derivative selected from a lower alkylene amide wherein the lower alkylene group together with the amide nitrogen forms a 5-, 6- or 7-membered ring, or a said lower alkylene amide substituted on the ring by hydroxy-(lower)alkyl or by lower alkanoyloxy-(lower) alkyl; an α-(lower)-carboalkoxy- or α-carboxy-substituted lower alkylamide; an α-(lower)carboalkoxy- or α-carboxy-substituted aryl-(lower) alkylamide in which aryl represents phenyl or 3-indolyl; an (amino or carbobenzyloxyamino)-(lower) alkylamide; an aryl-(lower)alkyl ester in which aryl represents phenyl or pyridyl; a lower alkanoyloxy-(lower) alkyl ester; a 3-phthalidyl ester; a (hydroxy, lower alkanoyloxy, or lower alkoxy)-substituted (lower)alkoxymethyl ester; a bicycloalkyloxycarbonyl-(lower)alkyl ester having up to 10 carbon atoms in the bicycloalkyl group in which bicycloalkyl represents unsubstituted or lower alkyl substituted bicyclo[2,2,1]heptyl; or a pharmaceutically acceptable salt thereof.

2. A compound which is a monofunctional derivative of an indoline-2-carboxylic acid of the formula

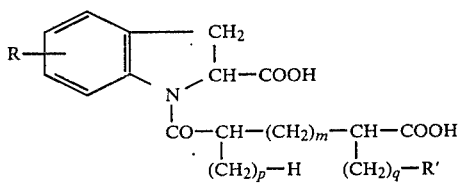

(II)

wherein R is hydrogen, alkyl or alkoxy with up to 4 carbon atoms, halogeno or trifluoromethyl; m is the integer 0 or 1; each of p and q is an integer from 0 to 2; and R' is hydrogen or R-phenyl in which R-phenyl represents phenyl unsubstituted or monosubstituted by alkyl or alkoxy with up to 4 carbon atoms, halogeno or trifluoromethyl; said derivative comprising a mono α-(lower)carbalkoxy- or α-carboxy-substituted lower alkylamide; a mono α-(lower)carbalkoxy- or α-carboxy-substituted aryl-(lower)alkylamide in which aryl represents phenyl; a mono aryl(lower)alkyl ester in which aryl represents phenyl or pyridyl; a mono bicycloalkyloxycarbonyl(lower)alkyl ester in which bicycloalkyl represents bornyl; a mono lower alkanoyloxy (lower)alkyl ester; or a pharmaceutically acceptable alkali metal or ammonium salt thereof.

3. A compound as claimed in claim 2 wherein the monofunctional derivative represents a benzyl ester; a pyridylmethyl ester; a pivaloyloxymethyl ester or a bornyloxycarbonylmethyl ester; or a pharmaceutically acceptable alkali metal or ammonium salt thereof.

4. A compound as claimed in claim 2 wherein the chirality corresponds to the formula IIa:

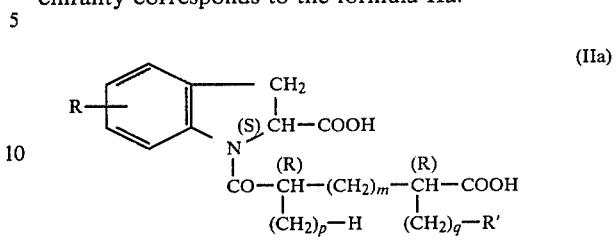

(IIa)

5. A compound as claimed in claim 1, in which Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_o$ is hydrogen or HPh; each of $R_1$, $R_2$ and $R_3$ is hydrogen or lower alkyl; and n is an integer from 2 to 8; or a pharmaceutically acceptable salt thereof.

6. A compound as claimed in claim 5, wherein Ph is 1,2-phenylene, unsubstituted or mono-substituted by lower alkyl, lower alkoxy, lower alkylenedioxy, hydroxy, halogeno or trifluoromethyl; $R_o$ is hydrogen or HPh; each of $R_1$, $R_2$ and $R_3$ is hydrogen or methyl; and n is an integer from 2 to 8; or a pharmaceutically acceptable salt thereof.

7. A compound as claimed in claim 2, in which R is hydrogen, methyl, methoxy, fluoro, chloro or trifluoromethyl; each of m and p is the integer 1; q is the integer 1 or 2; and R' is hydrogen or phenyl.

8. A compound as claimed in claim 2, wherein R is in the 5-indoline-position.

9. A compound as claimed in claim 2, in the form of its 2S-carboxy-indoline chiral epimer.

10. A compound as claimed in claim 2, and being 1-[4-(pivaloyloxymethoxycarbonyl)-2R,4R-dimethylbutanoyl]-indoline-2S-carboxylic acid; or a pharmaceutically acceptable alkali metal or ammonium salt thereof.

11. A compound as claimed in claim 2, and being 1-[4-(l-bornyloxycarbonylmethoxycarbonyl)-2R,4R-dimethylbutanoyl]-indoline-2S-carboxlic acid or a pharmaceutically acceptable alkali metal or ammonium salt thereof.

12. A compound as claimed in claim 2, and being 1-[4-(3-pyridylmethoxycarbonyl)-2R,4R-dimethylbutanoyl]-indoline-2S-carboxylic acid or a pharmaceutically acceptable acid addition, alkali metal or ammonium salt thereof.

13. A compound as claimed in claim 2 and being pivaloyloxymethyl 1-[4-carboxy-2R,4R-dimethylbutanoyl]-indoline-2S-carboxylate or a pharmaceutically acceptable alkali metal or ammonium salt thereof.

14. An antihypertensive or cardioactive pharmaceutical composition comprising a correspondingly effective amount of a compound as claimed in claim 1, together with a pharmaceutical excipient.

15. A method of treating hypertension or congestive heart failure in mammals, which consists in administering to said mammals in need thereof, an effective amount of a composition claimed in claim 14.

* * * * *